United States Patent
Janiga et al.

(10) Patent No.: US 9,988,385 B2
(45) Date of Patent: Jun. 5, 2018

(54) STRONGLY FLUORESCENT HETEROCYCLES AND A METHOD FOR THEIR SYNTHESIS

(71) Applicant: INSTYTUT CHEMII ORGANICZNEJ POLSKIEJ AKADEMII NAUK, Warsaw (PL)

(72) Inventors: Anita Janiga, Wlosienica (PL); Maciej Krzeszewski, Pila (PL); Daniel Gryko, Warsaw (PL)

(73) Assignee: INSTYTUT CHEMII ORGANICZNEJ POLSKIEJ AKADEMII NAUK, Warsaw (PL)

( * ) Notice: Subject to any disclaimer, the term of this patent is extended or adjusted under 35 U.S.C. 154(b) by 0 days. days.

(21) Appl. No.: 14/440,207

(22) PCT Filed: Nov. 5, 2013

(86) PCT No.: PCT/PL2013/050025
§ 371 (c)(1),
(2) Date: May 1, 2015

(87) PCT Pub. No.: WO2014/070029
PCT Pub. Date: May 8, 2014

(65) Prior Publication Data
US 2015/0246921 A1    Sep. 3, 2015

(30) Foreign Application Priority Data
Nov. 5, 2012 (PL) .......................... 401473

(51) Int. Cl.
*C07D 487/04* (2006.01)
*C09K 11/06* (2006.01)
(Continued)

(52) U.S. Cl.
CPC ............ *C07D 487/04* (2013.01); *C09B 57/00* (2013.01); *C09K 11/06* (2013.01);
(Continued)

(58) Field of Classification Search
CPC ....... C07D 487/04; C09B 57/00; C09K 11/06; C09K 2211/1007; C09K 2211/102; H01L 51/0072
(Continued)

(56) References Cited

FOREIGN PATENT DOCUMENTS

EP    1 087 005 A1    3/2001
JP    62-205080       9/1987
(Continued)

OTHER PUBLICATIONS

Hunkler, D. et al. Chemie des cis-Triaza-tris-σ-homobenzols. 3σ_3π-Isomerisierung zum 1,4,7-Triaza-2,5,8-cyclonanatrien-Gerüst. Angewandte Chemie. 1975, vol. 87, p. 350.*
(Continued)

*Primary Examiner* — Daniel R Carcanague
(74) *Attorney, Agent, or Firm* — Oblon, McClelland, Maier & Neustadt, L.L.P.

(57) ABSTRACT

This invention provides 1,4-dihydropyrrolo[3,2-b]pyrrole derivatives which can be used as strongly fluorescent compounds and a one-stage method for their synthesis from simple substrates.

20 Claims, 1 Drawing Sheet

Figure 1:
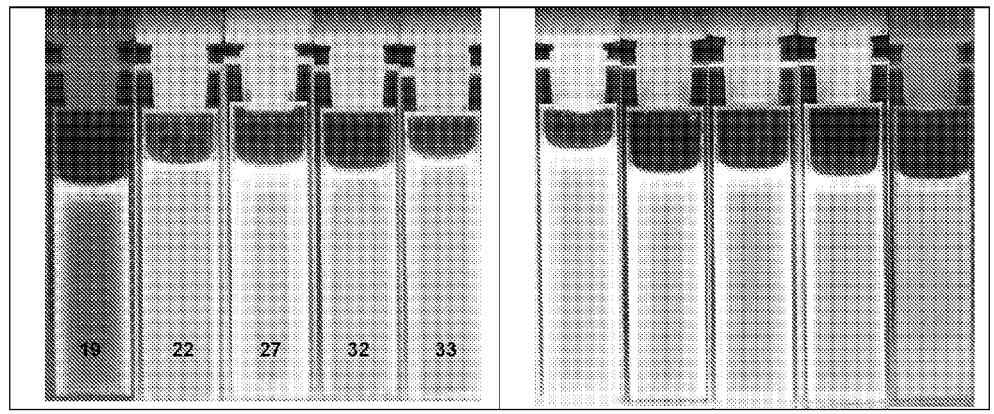

(51) Int. Cl.
    C09B 57/00      (2006.01)
    H01L 51/00      (2006.01)
(52) U.S. Cl.
    CPC .. *H01L 51/0072* (2013.01); *C09K 2211/1007* (2013.01); *C09K 2211/1029* (2013.01)
(58) Field of Classification Search
    USPC .................................................... 546/256
    See application file for complete search history.

(56)            References Cited

FOREIGN PATENT DOCUMENTS

| JP | 62-207275 | | 9/1987 |
|---|---|---|---|
| JP | 62-207276 | | 9/1987 |
| JP | 62-212389 | | 9/1987 |
| JP | 63-112618 | A | 5/1988 |
| JP | 2010-238880 | | 10/2010 |
| JP | 2010-238880 | A * | 10/2010 |
| WO | WO 2007/003520 | A1 | 1/2007 |
| WO | WO 2011/132866 | A1 | 10/2011 |

OTHER PUBLICATIONS

American Chemical Society (Dunn, PJ. et al. Green Chemistry Principle #8. ACS What is Green Chemistry. Accessed from ACS Website on Jan. 8, 2016.*
Hunkler, D. et al. Chemie des cis-Triaza-tris-σ-homobenzols. 3σ_3π-Isomerisierung zum 1,4,7-Triaza-2,5,8-cyclonanatrien-Gerüst Angewandte Chemie. 1975, vol. 87, p. 350.*
Mukai, T. et al. Physicochemical Properties of 3,6-di-t-butyl-1,4-dihydropyrrolo[3,2-b]-pyrrole and its N-methoxycarbonyl derivatives. Chemistry Letters. 1984, p. 2034.*
Dieck, T. et al. Glyoxal as a synthone. III. A simple synthesis of aminopyrroles and of dihydropyrrolo[3,2-b]pyrroles. Chemische Berichte. 1989, p. 129.*
Unverified Machine Translation of Japanese patent application JP2010238880 (Oct. 21, 2010). Proquest. (Year: 2010).*
Unverified Machine Translation of office action dated Aug. 15, 2017 in corresponding Japanese application 2015540634. (Year: 2017).*
International Search Report dated Apr. 9, 2014 in PCT/PL2013/050025 filed on Nov. 5, 2013.
Shoji Tanaka, et al., 1,4-Dihydropyrrolo[3,2-b]pyrrole: The Electronic Structure Elucidated by Photoelectron Spectroscopy, Bulletin of the Chemical Society of Japan, vol. 60, No. 6, XP55107513, 1987, pp. 1981-1983.
Heindirk Tom Dieck, et al., "Glyoxal als Synthom, III Eine Einfache Synthese von Aminopyrrolen and Dihydropyrrolo[3,2-b]pyrrolen", Chemische Berichte, vol. 122, No. 1, 1989, XP55104780, pp. 129-131.
Prinzbach H., "Vortragsreferate-Chemische Geselschaft Zürich", Chimia, Schweizerische Chemische Gesellschaft, CH, vol. 33, No. 9, 1979, XP008167738, pp. 332-334.
Florian Rörsch et al., Nonacidic Inhibitors of Human Microsomal Prostaglandin Synthase 1 (mPGES 1) Identified by a Multistep Virtual Screening Protocol, Journal of Medicinal Chemistry, vol. 53, No. 2, 2010, pp. 911-915.
Kyosuke Satake, et al., "Physicochemical Properties of 3,6-Dl-t-BUTYL-1,4-Dihydropyrrolo[3,2-b]-pyrrole and its N-Methoxycarbonyl Derivatives", Chemistry Letters, The Chemical Society of Japan 1984, No. 12, 1984, XP 55104786, pp. 2033-2036.
Tsutomu Kumagai, et al., "Synthesis of 1,4-dihydropyrrolo[3,2-b]pyrrole", Tetrahedron Letters, vol. 25, No. 49, XP55107434, pp. 5669-5672.
E Gelens, et al, "Efficient Library Synthesis of Imidazoles using a Multicomponent Reaction and Microwave Irradiation", Molecular Diversity, vol. 10, No. 1, 2006, XP019258512, pp. 17-22.
Anita Janiga, et al., "Synthesis and Optical Properties, of Tetraaryl-1,4-dihydropyrrolo[3,2-b]pyrroles", Asian Journal of Organic Chemistry, vol. 2, No. 5, XP55105878, 2013, pp. 411-415.
Office Action dated Aug. 15, 2017 issued in corresponding Japanese patent application No. 2015-540534.
Tanaka et al. Synthese and physikalische Eigenschaften von 3,6-Di-tert butyl-1, 4-diazapentalen, *Angewandte Chemie*, 1988, 100, (8), pp. 1134-1135.
Miyamoto et al. "Electrochemistry of New Heteroaromatic Compounds of Pyrrolopyrrole" *Journal of the Electrochemical Society*, 1991, vol. 138 (7). pp. 2003-2008.
Oyama et al. "Electropolymerization of Fused Pyrroles as New Heteroaromatic Polymers", *Synthetic Metals*, (1989), 28(1-2), pp. 193-198.
Oyama et al. "Electropolymerization of N,N'-dimethyl-1,4-dihydropyrrolo[3,2-b] pyrrole: A New Heteroaromatic Polymer" *Journal of the Chemical Society* Perkin Transactions 2: Physical Organic Chemistry, 1988, (6), pp. 833-838.
Oyama et al. "Electrochemical Studies of Fused-Pyrrole Systems", *Synthetic Metals*, (1987), 20(2), pp., 245-258.
Prinzbach et al. "Chemie descis-Triaza-tris-σ-homobenzols, 3σ→3π Isomerisierung zum 1,4,7-Triaza-2,5,8-cyclononatrien-Geruest", *Angewan dte Chemie*, 1975, 87, No. 9, pp. 349-350.

* cited by examiner

STRONGLY FLUORESCENT HETEROCYCLES AND A METHOD FOR THEIR SYNTHESIS

This invention provides the novel electron-rich heterocycles possessing unique structure and properties, which can be used as strongly fluorescent compounds and the one-stage method of their synthesis from simple substrates.

There is a requirement for new strongly fluorescent materials, due to the development of fluorometric techniques and intensification of their use in modern biomedical techniques and in diagnostics (e.g. optical imaging). Moreover the development of compounds, which display high fluorescent quantum yields is particularly desirable.

Under such circumstances, invented 1,4-dihydropyrrolo[3,2-b]pyrroles, which possess superb optical properties, have the potential to be molecule of choice for above applications.

The subject mater of invention is a compound of formula (I):

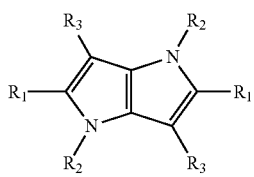

(I)

wherein $R^1$, $R^2$ and $R^3$ each independently stands for hydrogen or optionally substituted: alkyl, aryl, arylethynylaryl or heteroaryl, with the exception of the compound of formula (I) wherein $R^1=R^2=R^3=H$.

The term "aryl" means, unless otherwise stated, unsubstituted benzene, naphthalene, fluorene, 9,9-dialkylfluorene, or anthracene as well as benzene ring possessing the following substituents in ortho, meta or para positions: CN, $CO_2Me$, $CO_2Et$, $SO_3H$, CHO, $CONH_2$, F, Cl, Br, I, $NO_2$, OMe, $OCH_2O$, $NH_2$, $NMe_2$, $SF_5$.

The term "heteroaryl" refers to five-membered or six-membered aromatic ring that contain at least one heteroatom selected from N, O, S and Se. Examples of heteroaryl groups include pyridine, furan, pyrrole, thiophene, oxazole, imidazole, thiazole, pyrimidine.

The term "arylethynylaryl" refers to two benzene rings linked by carbon-carbon triple bond, possessing such substituents as: $NO_2$, CN, OMe, $SO_2Me$, $SO_3H$, F, Cl, Br, I, CHO, COOH, $CONH_2$, $SF_5$.

The term "alkyl" by itself or as part of another substituent, means, unless otherwise stated, a straight or branched chain with general formula: $C_nH_{2n+1}$ e.g. methyl, ethyl, n-propyl, isopropyl, n-butyl and tert-butyl.

Preferably, $R^3$ is hydrogen atom. Also preferably, $R^1$ and $R^2$, each independently, are aryl or heteroaryl substituents.

Especially preferably, $R^1$ and $R^2$ are derivatives of benzene, optionally substituted in ortho, meta, para position with a member selected from: $NO_2$, CN, OMe, $SO_2Me$, $SO_3H$, F, Cl, Br, I, CHO, COOH, $CONH_2$.

Preferably, compounds according to the invention have general formula (II):

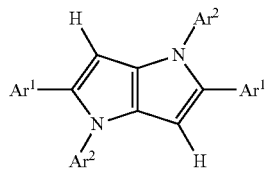

(II)

wherein $Ar^1$ and $Ar^2$ each independently stands for optionally substituted: aryl or heteroaryl, as defined above.

Preferably, compounds according to the invention have general formula III or IV:

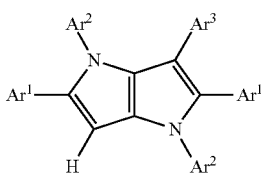

(III)

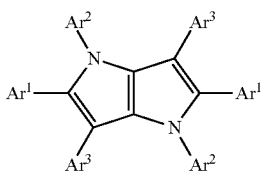

(IV)

wherein $Ar^1$, $Ar^2$ and $Ar^3$ each independently stands for optionally substituted: aryl or heteroaryl, as defined above.

Preferably, compounds according to the invention have general formula V:

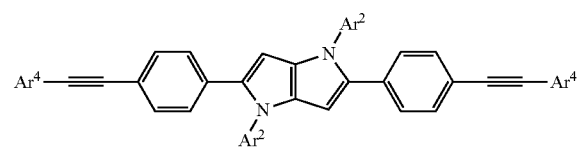

V wherein $Ar^2$ and $Ar^4$ each independently stands for optionally substituted: aryl or heteroaryl, as defined above.

Preferably, the compound according to the invention is selected from the group consisting of: compounds 1-15, compounds 16-26 (i.e. compound possessing general formula II), compounds 27-34 (i.e. compounds possessing general formulas III or IV) and compounds 35-39 (i.e. compound possessing general formula V), which have been enumerated and depicted below:

2,5-diphenyl-1,4-bis(4-methylphenyl)-1,4-dihydropyrrolo[3,2-b]pyrrole (1),
1,2,4,5-tetra(4-methylphenyl)-1,4-dihydropyrrolo[3,2-b]pyrrole (2),
2,5-di(naphthalen-1-yl)-1,4-bis(4-methylphenyl)-1,4-dihydropyrrolo[3,2-b]pyrrole (3),
2,5-di(anthracen-9-yl)-1,4-bis(4-octylphenyl)-1,4-dihydropyrrolo[3,2-b]pyrrole (4),
2,5-bis(4-cyanophenyl)-1,4-bis(4-methylphenyl)-1,4-dihydropyrrolo[3,2-b]pyrrole (5),
2,5-bis(3-cyanophenyl)-1,4-bis(4-methylphenyl)-1,4-dihydropyrrolo[3,2-b]pyrrole (6),
2,5-bis(2-cyanophenyl)-1,4-bis(4-methylphenyl)-1,4-dihydropyrrolo[3,2-b]pyrrole (7), 1,4-bis(4-bromophenyl)-2,5-bis(4-methylphenyl)-1,4-dihydropyrrolo[3,2-b]pyrrole (8),
2,5-bis(4-methoxyphenyl)-1,4-bis(4-methylphenyl)-1,4-dihydropyrrolo[3,2-b]pyrrole (9),
2,5-bis(benzo[d][1,3]dioxol-5-yl)-1,4-bis(4-methylphenyl)-1,4-dihydropyrrolo[3,2-b]pyrrole (10),
1,4-bis(4-chlorophenyl)-2,5-bis(4-cyanophenyl)-1,4-dihydropyrrolo[3,2-b]pyrrole (11),
2,5-bis(4-fluorophenyl)-1,4-bis(4-methoxyphenyl)-1,4-dihydropyrrolo[3,2-b]pyrrole (12),
1,4-bis(4-nitrophenyl)-2,5-bis(4-methylphenyl)-1,4-dihydropyrrolo[3,2-b]pyrrole (13),
2,5-bis(3-nitrophenyl)-1,4-bis(4-octylphenyl)-1,4-dihydropyrrolo[3,2-b]pyrrole (14),
2,5-di(pyridin-3-yl)-1,4-bis(4-methylphenyl)-1,4-dihydropyrrolo[3,2-b]pyrrole (15),
1,4-bis(4-methylphenyl)-2,5-bis(4-((trimethylsilyl)ethynyl)phenyl)-1,4-dihydropyrrolo[3,2-b]pyrrole (16),
2,5-bis(2-bromophenyl)-1,4-bis(4-methylphenyl)-1,4-dihydropyrrolo[3,2-b]pyrrole (17),
2,5-bis(2-methoxyphenyl)-1,4-bis(4-methylphenyl)-1,4-dihydropyrrolo[3,2-b]pyrrole (18),
2,5-bis(2-(allyloxy)phenyl)-1,4-bis(4-methylphenyl)-1,4-dihydropyrrolo[3,2-b]pyrrole (19),
1,4-bis(4-methylphenyl)-2,5-bis(4-(pentafluoro-$\lambda^6$-sulfanyl)phenyl)-1,4-dihydropyrrolo[3,2-b]pyrrole (20),
1,2,4,5-tetrakis(4-(pentafluoro-$\lambda^6$-sulfanyl)phenyl)-1,4-dihydropyrrolo[3,2-b]pyrrole (21),
1,4-bis(4-bromophenyl)-2,5-bis(4-cyanophenyl)-1,4-dihydropyrrolo[3,2-b]pyrrole (22),
2,5-bis(4-bromo-2-nitrophenyl)-1,4-bis(4-hexylphenyl)-1,4-dihydropyrrolo[3,2-b]pyrrole (23),
2,5-bis(benzo[b]thiophen-2-yl)-bis(4-methylphenyl)-1,4-dihydropyrrolo[3,2-b]pyrrole (24),
2,5-di(benzofuran-2-yl)-1,4-bis(4-methylphenyl)-1,4-dihydropyrrolo[3,2-b]pyrrole (25),
1,4-bis(4-methylphenyl)-2,5-bis(thiazol-2-yl)-1,4-dihydropyrrolo[3,2-b]pyrrole (26),
2,5-bis(4-cyanophenyl)-3-(9,9-dioctyl-9H-fluoren-3-yl)-1,4-bis(4-methylphenyl)-dihydropyrrolo[3,2-b]pyrrole (27),
2,5-bis(4-cyanophenyl)-1,4-bis(4-methylphenyl)-3-(4-nitrophenyl)-dihydropyrrolo[3,2-b]pyrrole (28),
2,5-bis(4-cyanophenyl)-1,4-bis(4-methylphenyl)-3,6-bis(4-nitrophenyl)-dihydropyrrolo[3,2-b]pyrrole (29),
2,5-bis(4-cyanophenyl)-1,4-bis(4-methylphenyl)-3,6-bis(4-(pentafluoro-$\lambda^6$-sulfanyl)phenyl)-1,4-dihydropyrrolo[3,2-b]pyrrole (30),
2,5-bis(4-cyanophenyl)-1,4-bis(4-methylphenyl)-3-(pyridin-3-yl)-1,4-dihydropyrrolo[3,2-b]pyrrole (31),
2,5-bis(4-cyanophenyl)-1,4-bis(4-methylphenyl)-3,6-di(pyridin-3-yl)-1,4-dihydropyrrolo[3,2-b]pyrrole (32),
2,3,5-tris(4-cyanophenyl)-1,4-bis(4-methylphenyl)-1,4-dihydropyrrolo[3,2-b]pyrrole (33),
2,5-bis(4-cyanophenyl)-3-(4-methoxyphenyl)-1,4-bis(4-methylphenyl)-1,4-dihydropyrrolo[3,2-b]pyrrole (34),
2,5-bis(4-(4-cyanoethynylphenyl)phenyl)-1,4-bis(4-methylphenyl)-1,4-dihydropyrrolo[3,2-b]pyrrole (35),
2,5-bis(4-(4-pentafluorothiophenyl)ethynylphenyl)-1,4-bis(4-methylphenyl)-1,4-dihydropyrrolo[3,2-b]pyrrole (36),
2,5-bis(4-(4-trifluoromethyl)ethynylphenyl)-1,4-bis(4-methylphenyl)-1,4-dihydropyrrolo[3,2-b]pyrrole (37),
2,5-bis(4-(3,5-di(trifluoromethyl)ethynylphenyl)-1,4-bis(4-methylphenyl)-1,4-dihydropyrrolo[3,2-b]pyrrole (38),
2,5-bis(4-(methoxy)ethynylphenyl)-1,4-bis(4-methylphenyl)-1,4-dihydropyrrolo[3,2-b]pyrrole (39).

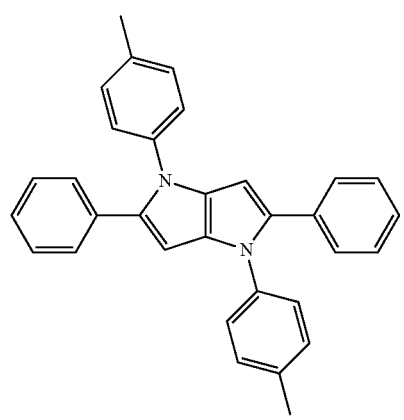

1

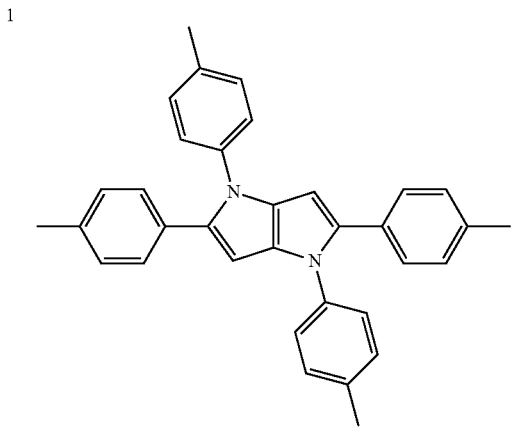

2

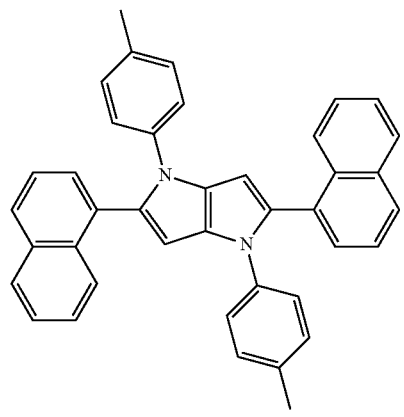

3

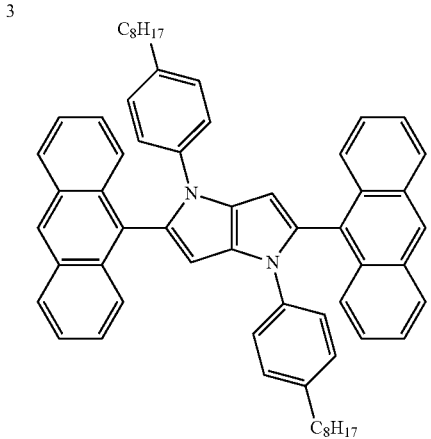

4

-continued
| | |
|---|---|
| 5 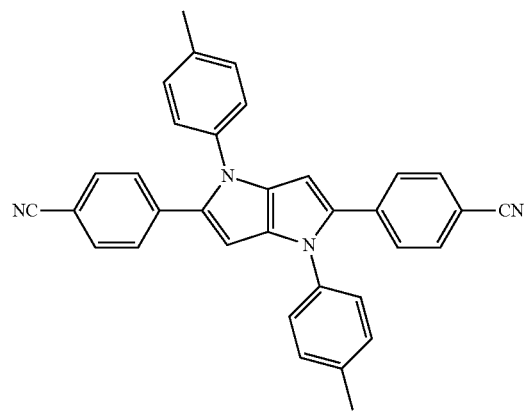 | 6 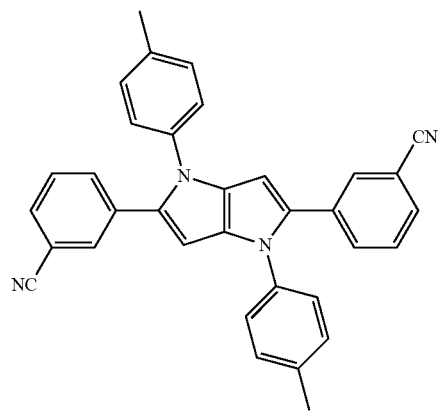 |
| 7 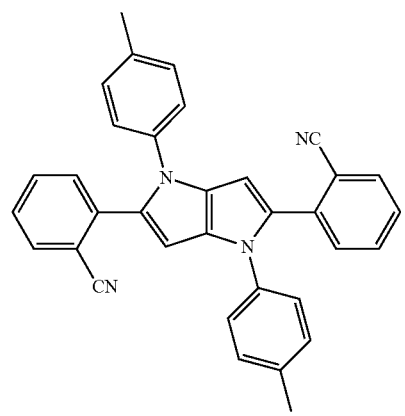 | 8 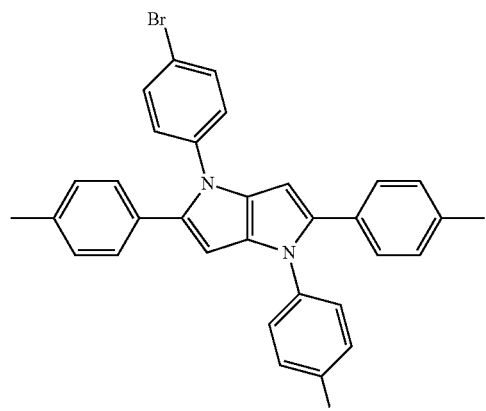 |
| 9 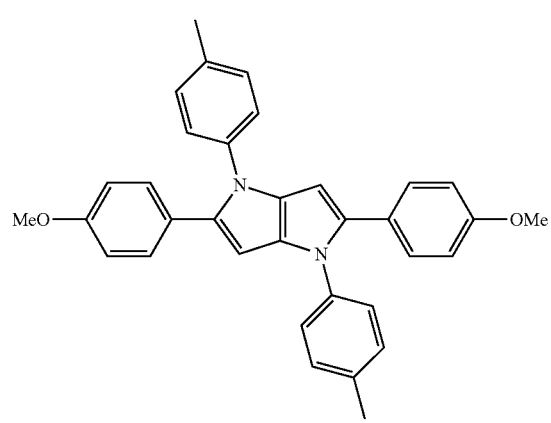 | 10 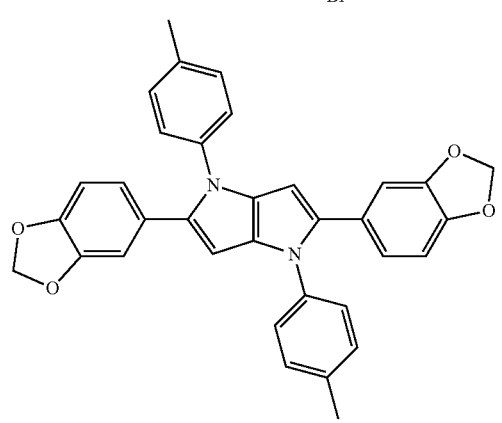 |
| 11 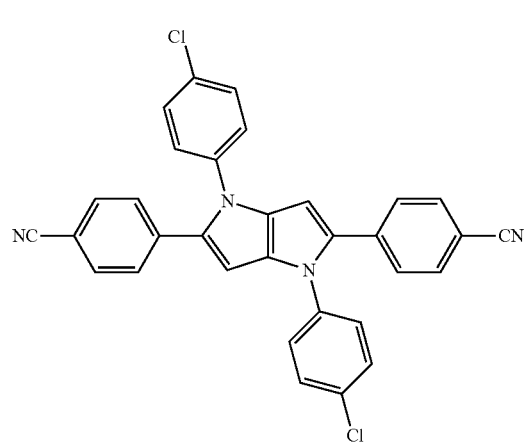 | 12 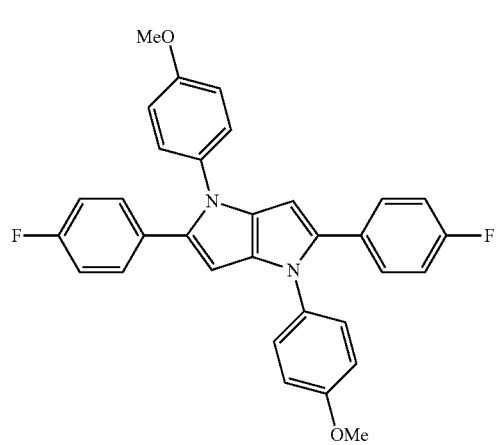 |

-continued
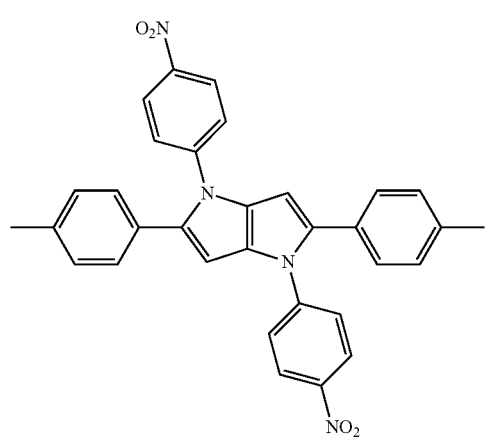
13
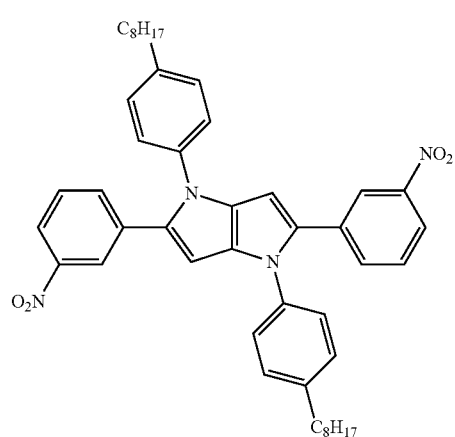
14
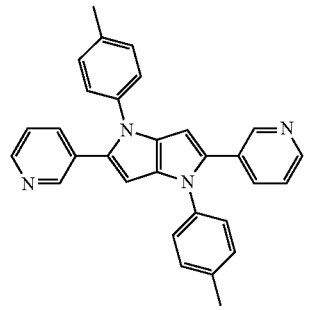
15
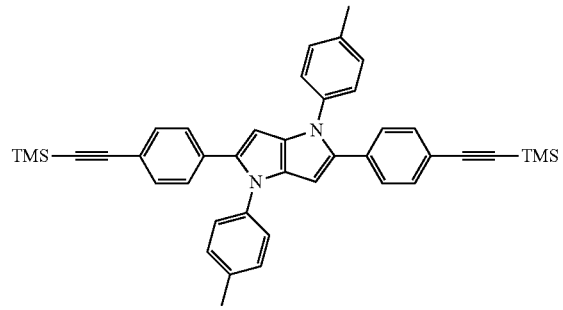
16
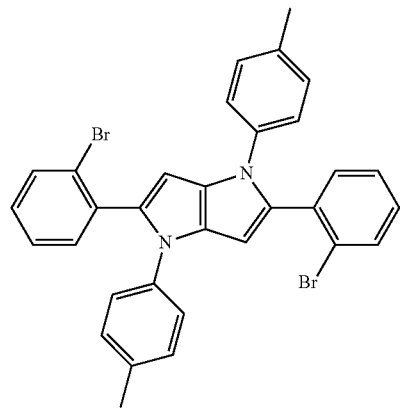
17
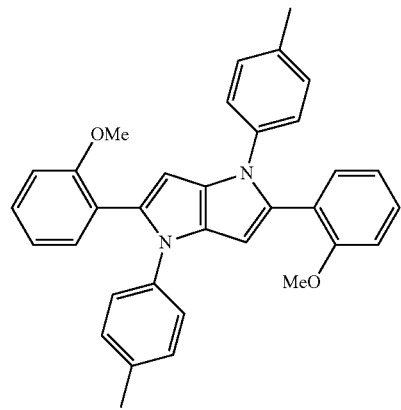
18
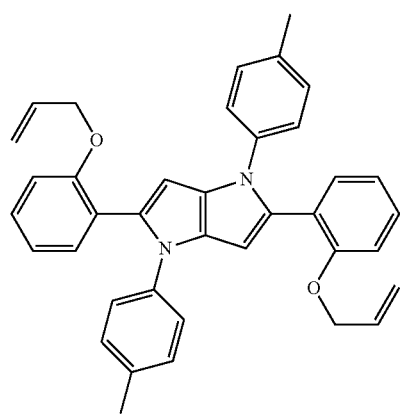
19
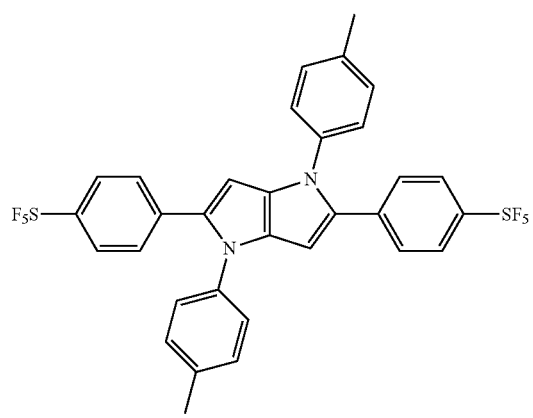
20

-continued
21
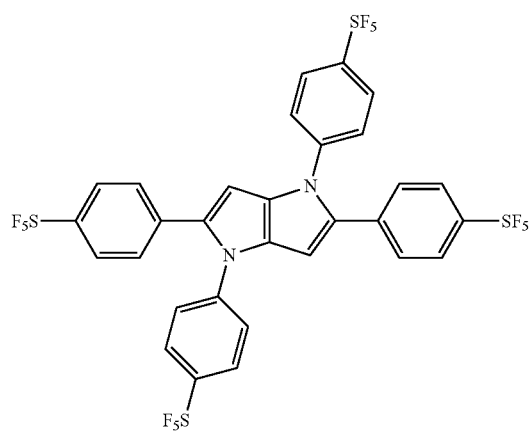
22
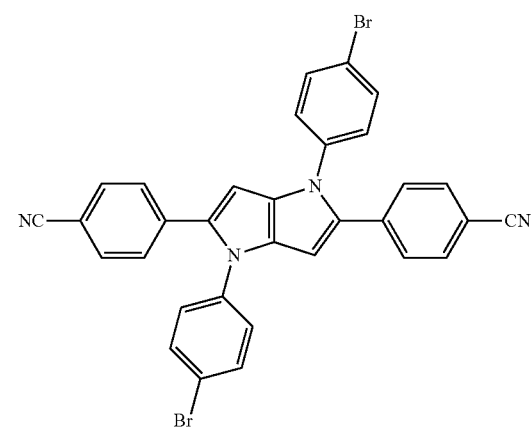
23
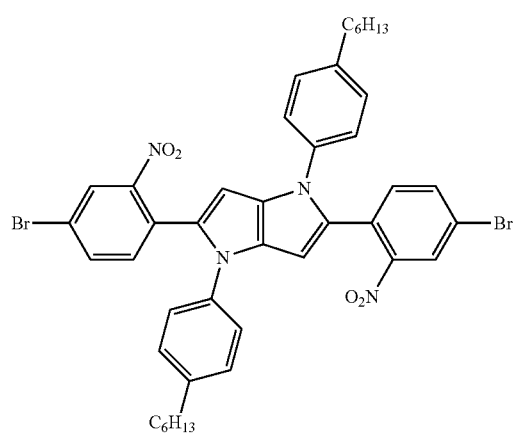
24
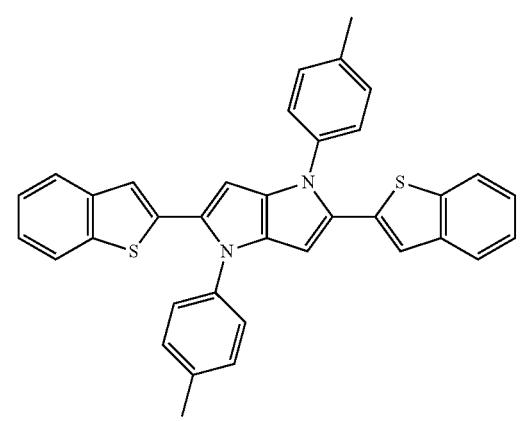
25
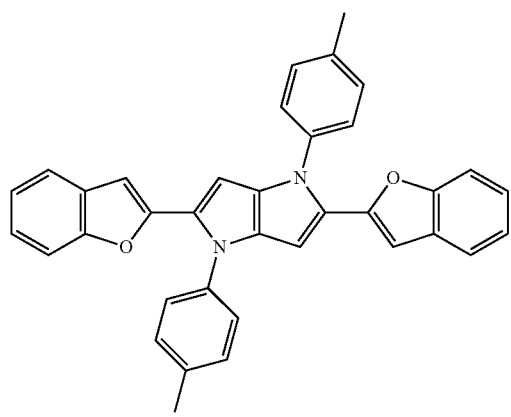
26
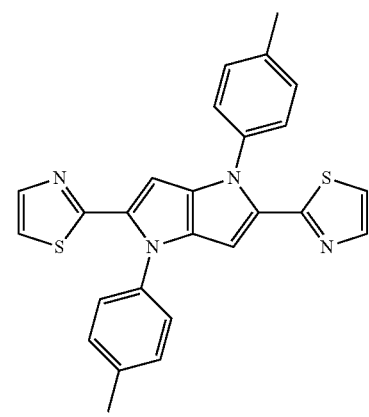

-continued
27
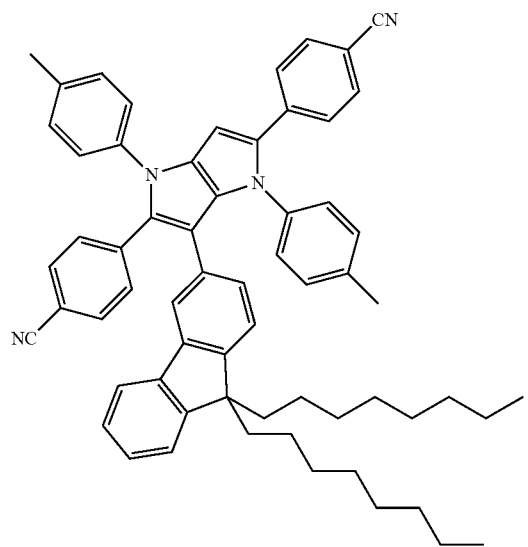
28
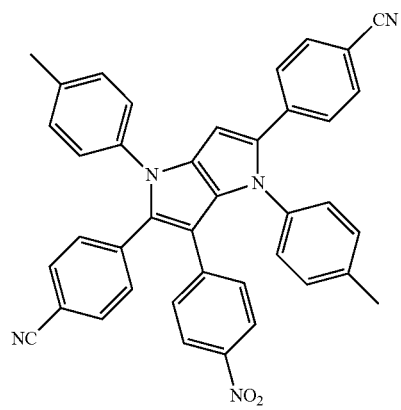
29
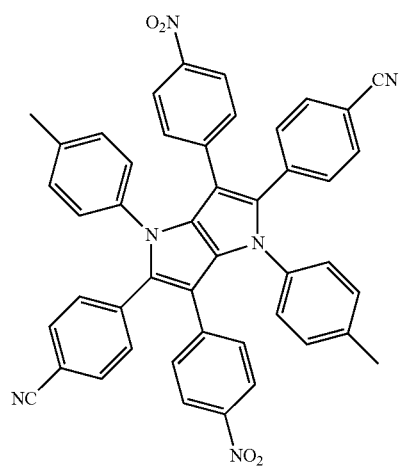
30
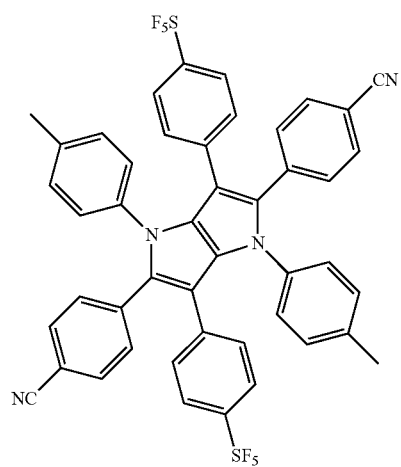
31
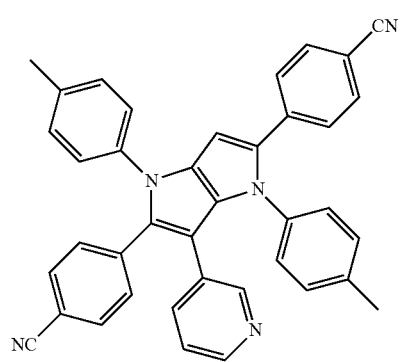
32
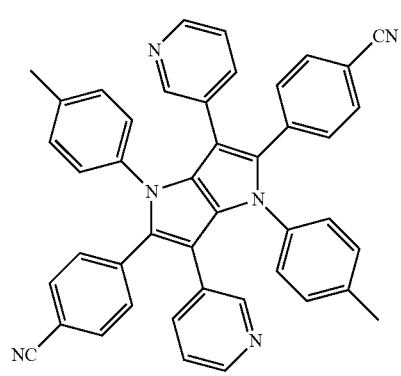

-continued
33
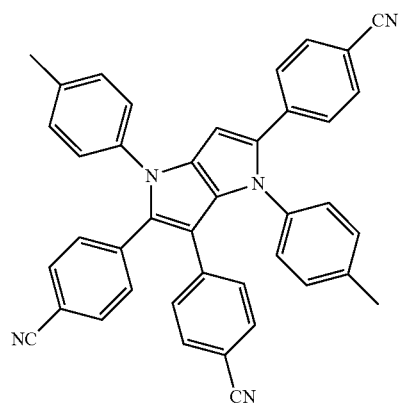
34
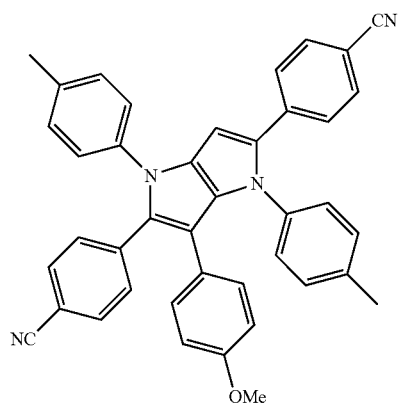
35
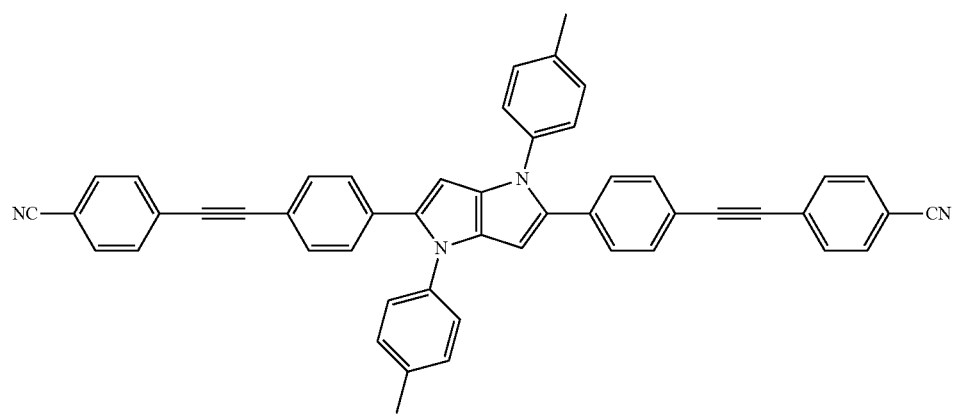
36
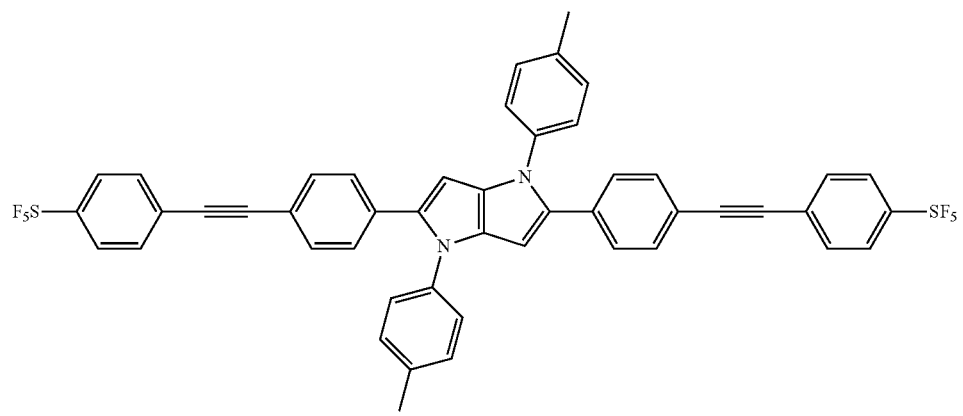
37
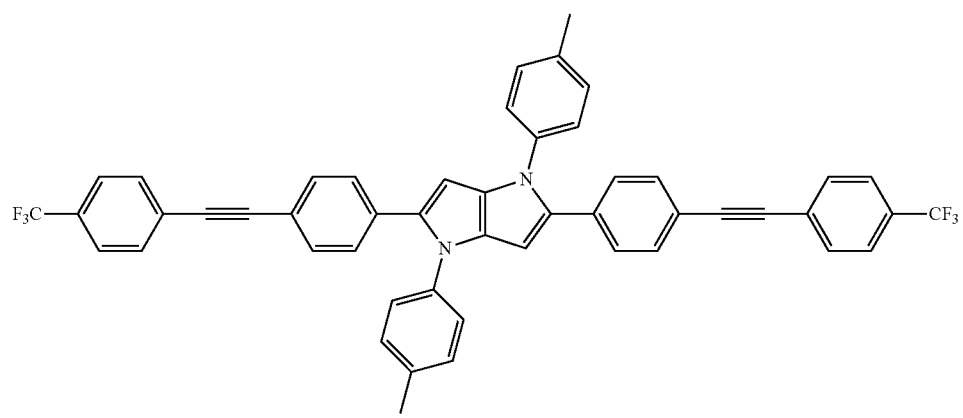

38

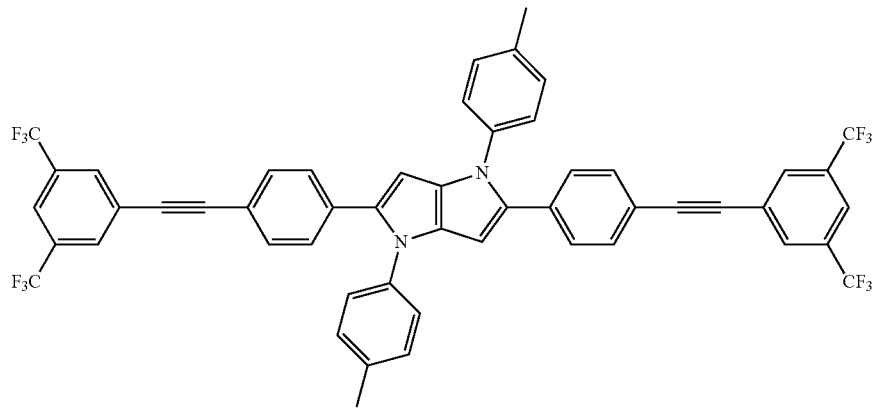

39

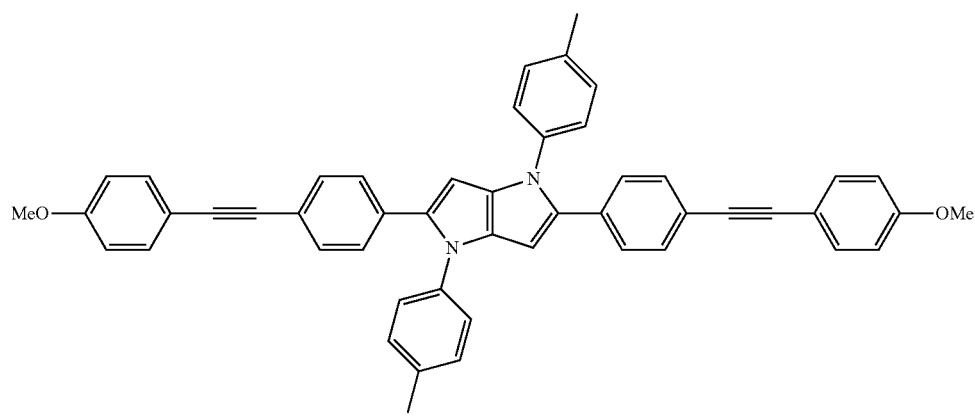

The next subject of the invention is the method of synthesis compound of formula (II):

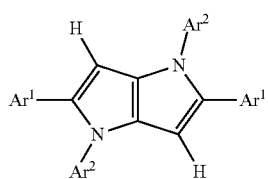

(II)

wherein Ar¹ and Ar² are substituents selected from aryl or heteroaryl. General procedure involves reaction of butane-2,3-dione with arylaldehyde with formula Ar¹CHO and arylamine with formula Ar²NH₂ in acidic conditions. Further isolation leads to compound II.

Preferably, the reaction is performed in acetic acid, particularly in glacial acetic acid. Further, the reaction may be carried out at temperature above 50° C. in particular around 100° C. Compound with a formula II precipitates from reaction mixture and further filtration affords pure product.

Preferably, the reaction is performed in the presence of Brønsted acid as catalyst, especially Brønsted acid with pK$_a$<2, in particular arylsulfonic acid, especially such as p-toluenosulfonic acid or benzenesulfonic acid. Further, the reaction may be carried out at room temperature or under heating, e.g. at a temperature of 50° C.-110° C. Compound with a formula (II) precipitates from reaction mixture and further filtration affords pure product.

This synthetic methodology has significant advantage over previous one. The yields of products are significantly (1.3-3) higher than without catalyst. This is especially pronounced if Ar¹ possess ortho substituents (entries 4, 5, 6).

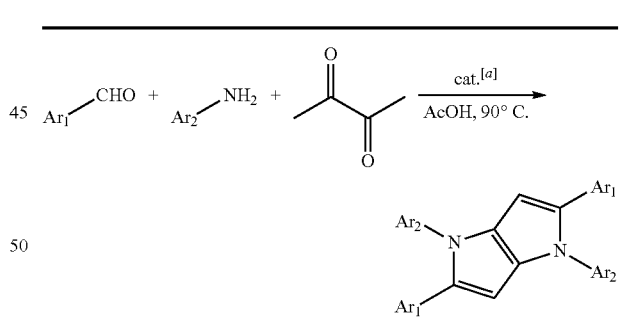

| entry | Ar₁ | Ar₂ | yield[b] [%] | yield[c] [%] |
|---|---|---|---|---|
| 1 | 4-NC-C₆H₄ | 4-Me-C₆H₄ | 30 | 37 |
| 2 | 3-NC-C₆H₄ | 4-Me-C₆H₄ | 28 | 34 |

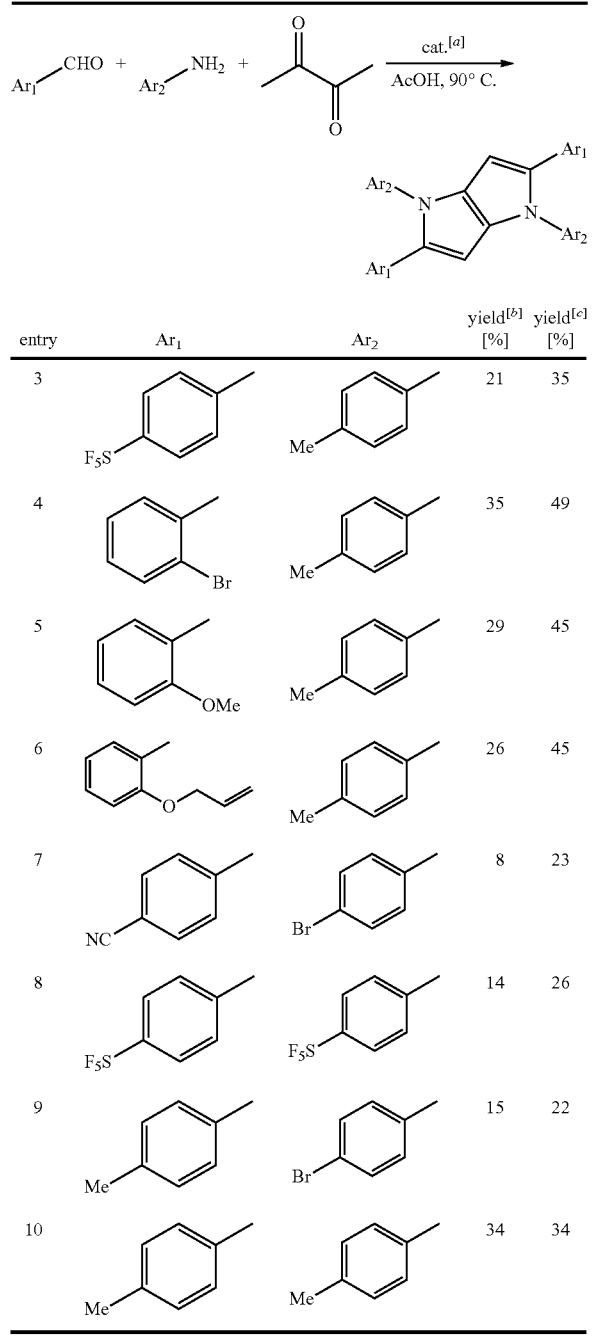

[a]cat.-pTsOH, benzenesulfonic acid
[b]isolated yield without catalyst.
[c]isolated yield after addition of catalyst to the reaction mixture.

The most characteristic feature of compounds synthesized according to the present invention is a strong absorption of UV and visible-light in range violet to greenish-blue. Their color oscillates between colorless, through yellow and orange to red (FIG. 1). Compounds of the invention, which possess electron-donating groups and halogens, are colorless. Moreover, all of synthesized compounds are fluorescent and they emit blue or violet light both in a solution and (what is very rare) in solid state. Few exceptions from this rule are compounds possessing NO2 group, which quenches fluorescence. However they possess very intense orange-red color in solid state, which makes them dyes. Moreover NO2 group decrease solubility of a dye in water or in organic solvents. Consequently they can be used as pigments, which is preferable from the point of view of industrial uses. Compounds synthesized according to the present invention possess strong absorption of light in a range 280-520 nm (molar absorption coefficient is 10000-71000 units). It means that in a various practical applications, less substance can be used with the same final effect. However the most important is fact that fluorescence quantum yields are very high (usually above 50%). Detailed optical parameters (i.e. absorption maxima, emission maxima, molar absorption coefficient and fluorescence quantum yield) are shown in Table 1. All, the most characteristic examples are presented there. Compounds synthesized according to the present invention are characterized by their quadrupolic structure what may influence on high value of two photon cross section, thus may be applied in two-photon excited fluorescence (TPEF) microscopy.

Compounds of the invention may be obtained in a multicomponent reaction from simple substrates i.e. aldehydes, amines and diacetyl. Acetic acid, which serves as a solvent as well as precipitation of a product from reaction mixture, make this synthetic process is operationally simple, fast, economic and ecologic.

The following examples exemplify the invention without limiting it.

EXAMPLE 1

General Synthetic Method (Compound of Formula II)

A variant carried out without catalyst:

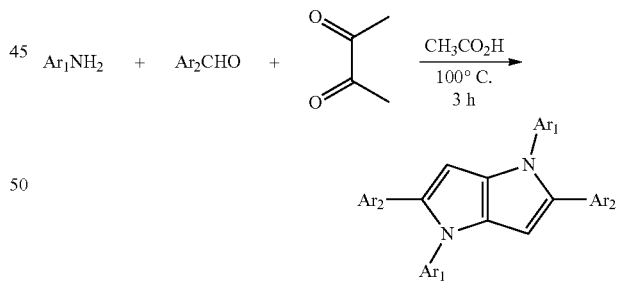

1-15

In a 25 ml round-bottom flask equipped with a reflux condenser and magnetic stirrer were placed 5 mL glacial acetic acid, butane-2,3-dione (1 mmol), arylamine (2 mmol), aldehyde (2 mmol). The resulting mixture was stirred at 100° C. for 3 h. Then reaction mixture was cooled to room temperature. Resulting precipitate was then filtered off and washed with cold glacial acetic acid. Recrystallization from AcOEt followed by drying under vacuum afforded pure product.

A variant carried out in presence of catalyst:

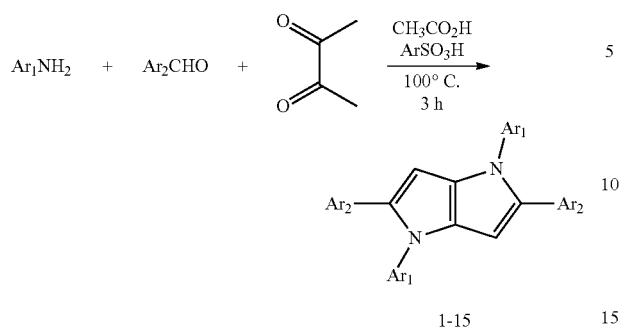

1-15

In a 25 ml round-bottom flask equipped with a reflux condenser and magnetic stirrer were placed 5 mL glacial acetic acid, butane-2,3-dione (1 mmol), arylamine (2 mmol), aldehyde (2 mmol) and p-toluenesulfonic acid (0.2 mmol). The resulting mixture was stirred at 100° C. for 3 h. Then reaction mixture was cooled to room temperature. Resulting precipitate was then filtered off and washed with cold glacial acetic acid. Recrystallization from AcOEt followed by drying under vacuum afforded pure product.

In examples 2-16 the syntheses of compounds 1-15 have been described.

EXAMPLE 2

2,5-diphenyl-1,4-bis(4-methylphenyl)-1,4-dihydropyrrolo[3,2-b]pyrrole (1)

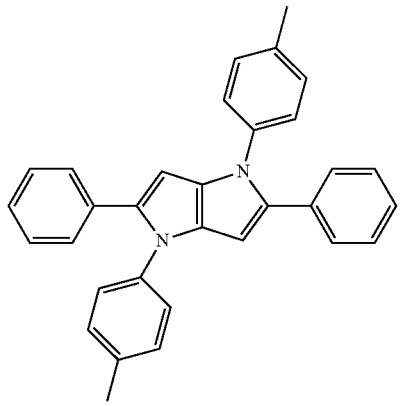 [SMILES: Cc1ccc(-n2c(-c3ccccc3)cc3c2cc(-c2ccccc2)n3-c2ccc(C)cc2)cc1]

Beige solid. Yield 145 mg (33%).[b] $R_f$=0.86 (SiO$_2$, AcOEt/hexanes, 1:4). Mp 239-244° C. (CH$_3$CO$_2$H). $^1$H NMR (500 MHz, CDCl$_3$) δ 7.22 (AA'XX', 41-1), 7.21 (AA'XX', 41-1), 7.19-7.13 (m, 10H), 6.38 (s, 2H), 2.36 (s, 6H). $^{13}$C NMR (125 MHz, CDCl$_3$) 6137.5, 135.7, 135.3, 133.8, 131.6, 129.6, 128.2, 128.1, 126.0, 125.0, 94.5, 21.0. HRMS (EI) calcd for C$_{32}$H$_{26}$N$_2$: 438.2096 [M$^+$]. found: 438.2100. Anal. calcd for C$_{32}$H$_{26}$N$_2$: C, 87.64; H, 5.98; N, 6.39. found: C, 87.79; H, 5.97; N, 6.40. $\lambda_{abs}$ (CH$_3$Cl, ε×10$^{-3}$) 348 (33) nm.

EXAMPLE 3

1,2,4,5-tetra(4-methylphenyl)-1,4-dihydropyrrolo[3,2-b]pyrrole (2)

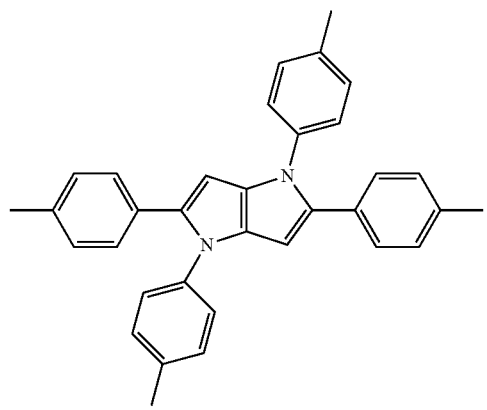

White solid. Yield 158 mg (34%).[b,c] $R_f$=0.71 (SiO$_2$, AcOEt/hexanes, 1:4). Mp 261-262° C. (CH$_3$CO$_2$H). $^1$H NMR (500 MHz, CDCl$_3$) δ 7.17 (AA'XX', 4H), 7.15 (AA'XX', 4H), 7.11 (AA'XX', 4H), 7.02 (AA'XX', 4H), 6.33 (s, 2H), 2.36 (s, 6H), 2.30 (s, 6H). $^{13}$C NMR (125 MHz, CDCl$_3$) δ 137.7, 135.7, 135.6, 135.1, 131.3, 131.0, 129.6, 128.8, 128.0, 125.0, 94.1, 21.1, 21.0. HRMS (EI) calcd for C$_{34}$H$_{30}$N$_2$: 466.2409 [M$^+$]. found: 466.2406. Anal. calcd for C$_{34}$H$_{30}$N$_2$: C, 87.52; H, 6.48; N, 6.00. found: C, 87.47; H, 6.43; N, 5.94. $\lambda_{abs}$ (CH$_2$Cl$_2$, ε×10$^{-3}$) 348 (37) nm.

EXAMPLE 4

2,5-di(naphthalen-1-yl)-1,4-bis(4-methylphenyl)-1,4-dihydropyrrolo[3,2-b]pyrrole (3)

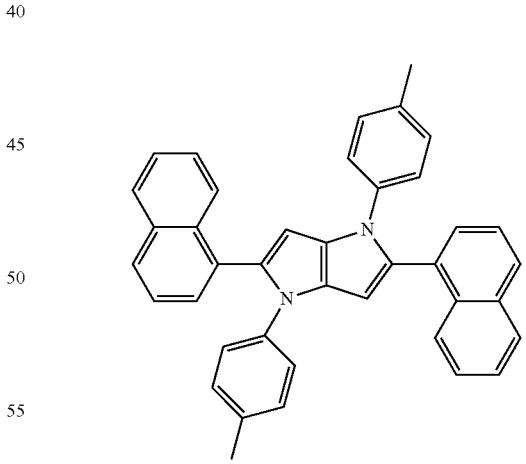

Yellow solid. Yield 270 mg (50%).[b] $R_f$=0.61 (SiO$_2$, AcOEt/hexanes, 1:2). Mp 249-252° C. (AcOEt). $^1$H NMR (500 MHz, CDCl$_3$) δ 8.26 (d, J=7.9 Hz, 2H), 7.84 (d, J=7.6 Hz, 2H), 7.77 (d, J=7.9 Hz, 2H), 7.46-7.32 (m, 8H), 7.10 (AA'XX', 4H), 6.95 (AA'XX', 4H), 6.55 (s, 2H), 2.23 (s, 6H). $^{13}$C NMR (500 MHz, CDCl$_3$) 6137.4, 134.6, 133.8, 132.9, 132.5, 131.7, 130.4, 129.4, 129.0, 128.0, 127.4, 126.6, 126.0, 125.7, 125.1, 123.9, 97.0, 20.9. HRMS (EI) calcd for C$_{40}$H$_{30}$N$_2$: 538.2409 [M$^+$]. found: 538.2419. Anal.

calcd for $C_{40}H_{30}N_2$: C, 89.19; H, 5.61; N, 5.20. found: C, 89.14; H, 5.70; N, 5.17. $\lambda_{abs}$ (toluene, $\epsilon \times 10^{-3}$) 377 (14) nm.

EXAMPLE 5

2,5-di(anthracen-9-yl)-1,4-bis(4-octylphenyl)-1,4-dihydropyrrolo[3,2-b]pyrrole (4)

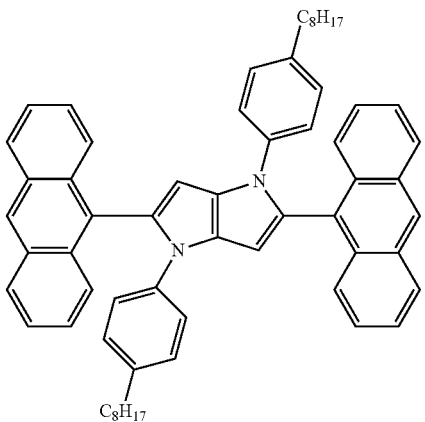

Orange solid. Yield 93 mg (11%).[b] $R_f$=0.74 (SiO$_2$, AcOEt/hexanes, 1:9). Mp 223-224° C. $^1$H NMR (500 MHz, CDCl$_3$) δ 8.46 (s, 2H), 8.22-8.14 (m, 4H), 8.03-7.94 (m, 4H), 7.47-7.34 (m, 8H), 7.01 (AA'XX', 4H), 6.72 (AA'XX', 4H), 6.61 (s, 2H), 2.37-2.24 (m, 4H), 1.32-1.39 (m, 4H), 1.20-1.27 (m, 4H), 1.14-1.19 (m, 12H), 1.05-1.13 (m, 4H), 0.83 (t, J=7.1 Hz, 6H). $^{13}$C NMR (500 MHz, CDCl$_3$) δ 139.3, 137.6, 132.3, 131.3, 130.1, 130.0, 128.9, 128.5, 128.2, 127.4, 127.2, 125.7, 125.1, 122.9, 98.3, 35.1, 31.8, 31.0, 29.3, 29.2, 29.1, 22.6, 14.1. HRMS (EI) calcd for ($C_{62}H_{62}N_2$), 834.4913 [M$^+$]. found, 834.4900. Anal. calcd for $C_{62}H_{62}N_2$: C, 89.16; H, 7.48; N, 3.35. Found: C, 89.15; H, 7.42; N, 3.29. $\lambda_{abs}$ (toluene $\epsilon \times 10^{-3}$) 387 (35) nm.

EXAMPLE 6

2,5-bis(4-cyanophenyl)-1,4-bis(4-methylphenyl)-1,4-dihydropyrrolo[3,2-b]pyrrole (5)

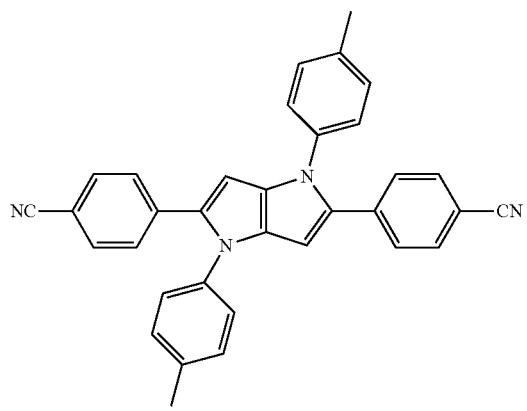 [SMILES: Cc1ccc(-n2c(-c3ccc(C#N)cc3)cc3c2cc(-c2ccc(C#N)cc2)n3-c2ccc(C)cc2)cc1]

Yellow-green solid. Yield 180 mg (37%).[c] $R_f$=0.65 (SiO$_2$, CH$_2$Cl$_2$). Mp 319-321° C. (AcOEt). $^1$H NMR (600 MHz, CDCl$_3$) δ 7.47 (AA'XX', 4H), 7.27 (AA'XX', 4H), 7.21 (AA'XX', 4H), 7.14 (AA'XX', 4H), 6.45 (s, 2H), 2.40 (s, 6H); $^{13}$C NMR (150 MHz, CDCl$_3$) δ 137.7, 136.7, 136.5, 135.0, 133.4, 131.9, 130.1, 127.8, 125.2, 119.1, 109.0, 95.8, 21.1. HRMS (FD-TOF) calcd for $C_{34}H_{24}N_4$: 488.2001 [M$^+$]. found: 488.2014. Anal. calcd for $C_{34}H_{24}N_4$: C, 83.58; H, 4.95; N, 11.47. found: C, 83.53; H, 4.97; N, 11.33. $\lambda_{abs}$ (CH$_2$Cl$_2$, $\epsilon \times 10^{-3}$) 405 (54) nm.

EXAMPLE 7

2,5-bis(3-cyanophenyl)-1,4-bis(4-methylphenyl)-1,4-dihydropyrrolo[3,2-b]pyrrole (6)

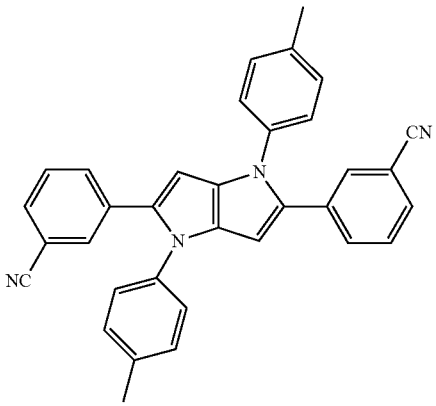 [SMILES: Cc1ccc(-n2c(-c3cccc(C#N)c3)cc3c2cc(-c2cccc(C#N)c2)n3-c2ccc(C)cc2)cc1]

Yellow solid. Yield 166 mg (34%).[c] $R_f$=0.52 (SiO$_2$, AcOEt/hexanes, 1:2). Mp 314-316° C. (AcOEt). $^1$H NMR (500 MHz, CDCl$_3$) δ 7.51 (t, J=1.5 Hz, 2H), 7.42 (dd, J=7.6, 1.4 Hz, 2H), 7.40-7.36 (m, 2H), 7.20 (AA'XX', 4H), 7.13 (AA'XX', 4H), 6.41 (s, 2H), 2.40 (s, 6H). $^{13}$C NMR (125 MHz, CDCl$_3$) δ 136.6, 136.4, 134.7, 134.0, 132.5, 132.0, 131.0, 130.1, 129.4, 128.9, 125.1, 118.7, 112.4, 95.3, 21.1. HRMS (ESI) calcd for $C_{34}H_{24}N_4$: 488.2001 [M$^+$]. found: 488.1999. Anal. calcd for $C_{34}H_{24}N_4$: C, 83.58; H, 4.95; N, 11.47. found: C, 83.73; H, 4.86; N, 11.45. $\lambda_{abs}$ (CH$_2$Cl$_2$, $\epsilon \times 10^{-3}$) 368 (33) nm.

EXAMPLE 8

2,5-bis(2-cyanophenyl)-1,4-bis(4-methylphenyl)-1,4-dihydropyrrolo[3,2-b]pyrrole (7)

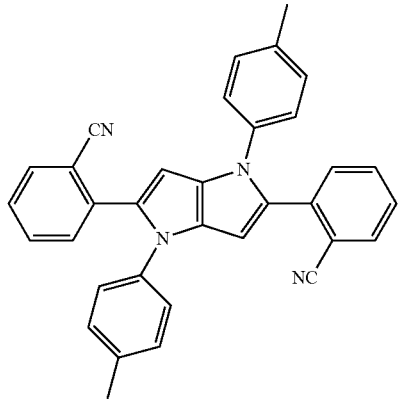 [SMILES: Cc1ccc(-n2c(-c3ccccc3C#N)cc3c2cc(-c2ccccc2C#N)n3-c2ccc(C)cc2)cc1]

Yellow solid. Yield 23 mg (5%).[b] $R_f$=0.37 (SiO$_2$, AcOEt/hexanes, 1:4). Mp 344-345° C. (AcOEt). $^1$H NMR (500 MHz, CDCl$_3$) δ 7.66 (dd, J=7.8, 1.1 Hz, 2H), 7.37 (dd, J=7.7, 1.3 Hz, 2H), 7.30-7.27 (m, 2H), 7.16-7.09 (m, 10H), 6.66 (s, 2H), 2.35 (s, 6H). $^{13}$C NMR (125 MHz, CDCl$_3$) δ

137.1, 136.6, 135.7, 133.7, 132.0, 131.9, 131.8, 131.1, 129.9, 126.7, 124.9, 118.8, 111.4, 97.2, 21.0. HRMS (EI) calcd for $C_{34}H_{24}N_4$: 488.1988 [M+]. found: 488.1989. Anal. calcd for $C_{34}H_{24}N_4$: C, 83.58; H, 4.95; N, 11.47. found: C, 83.50; H, 4.91; N, 11.54. $\lambda_{abs}$ (toluene, ε×10$^{-3}$) 388 (10) nm.

EXAMPLE 9

1,4-bis(4-bromophenyl)-2,5-bis(4-methylphenyl)-1,4-dihydropyrrolo[3,2-b]pyrrole (8)

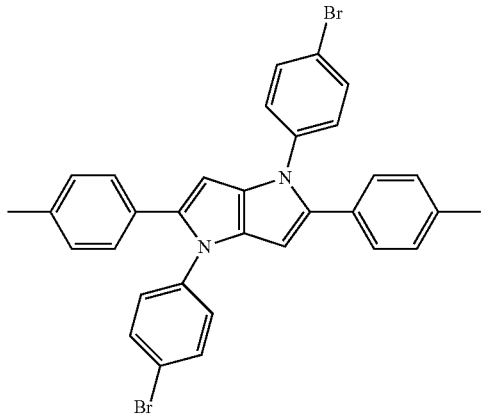

White solid. Yield 133 mg (22%).[c] $R_f$=0.71 (SiO$_2$, AcOEt/hexanes, 1:4). Mp 297-298° C. (AcOEt). $^1$H NMR (500 MHz, CDCl$_3$) δ 7.46 (AA'XX', 4H), 7.14 (AA'XX', 4H), 7.09 (AA'XX', 4H), 7.05 (AA'XX', 4H), 6.34 (s, 2H), 2.32 (s, 6H). $^{13}$C NMR (125 MHz, CDCl$_3$) δ 139.1, 136.3, 135.8, 132.2, 131.0, 130.3, 129.1, 128.2, 126.6, 118.9, 94.9, 21.2. HRMS (EI) calcd for $C_{32}H_{24}Br_2N_2$: 594.0306 [M+]. found: 594.0322. Anal. calcd for $C_{32}H_{24}Br_2N_2$: C, 64.45; H, 4.06; Br, 26.8; N, 4.7. found: C, 64.44; H, 4.15; Br, 26.75; N, 4.60. $\lambda_{abs}$ (CHCl$_3$, ε×10$^{-3}$) 304 (35), 348 (33) nm.

EXAMPLE 10

2,5-bis(4-methoxyphenyl)-1,4-bis(4-methylphenyl)-1,4-dihydropyrrolo[3,2-b]pyrrole (9)

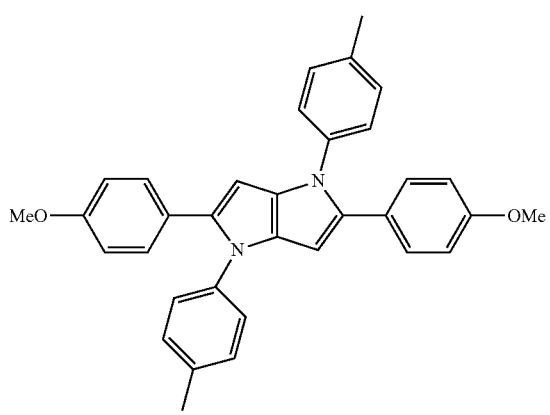 [SMILES: COc1ccc(-c2cc3c(cc(-c4ccc(OC)cc4)n3-c3ccc(C)cc3)n2-c2ccc(C)cc2)cc1]

White solid. Yield 77 mg (15%).[b] $R_f$=0.60 (SiO$_2$, AcOEt/hexanes, 1:2). Mp 241-242° C. (CH$_3$CO$_2$H). $^1$H NMR (500 MHz, C$_6$D$_6$) δ 7.31 (AA'XX', 4H), 7.28 (AA'XX', 4H), 6.89 (AA'XX', 4H), 6.69 (AA'XX', 4H), 6.54 (s, 2H), 3.25 (s, 6H), 2.04 (s, 6H). $^{13}$C NMR (125 MHz, C$_6$D$_6$) δ 158.7, 138.6, 135.6, 135.0, 132.1, 130.0, 129.8, 125.6, 114.1, 94.8, 54.7, 20.8. HRMS (FD) calcd for $C_{34}H_{30}N_2O_2$: 498.2307 [M+]. found: 498.2307. Anal. calcd for $C_{34}H_{30}N_2O_2$: C, 81.90; H, 6.06; N, 5.62. found: C, 81.73; H, 5.87; N, 5.51. $\lambda_{abs}$ (toluene, ε×10$^{-3}$) 300 (27), 348 (36) nm.

EXAMPLE 11

2,5-bis(benzo[d][1,3]dioxol-5-yl)-1,4-bis(4-methylphenyl)-1,4-dihydropyrrolo[3,2-b]pyrrole (10)

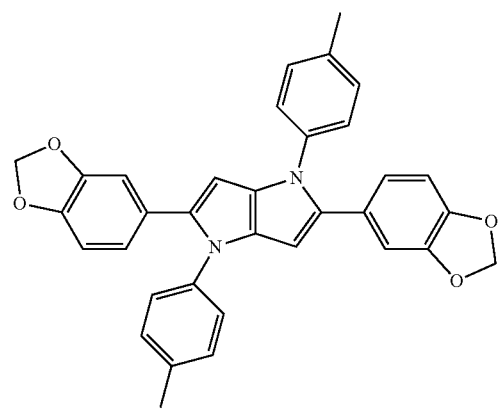 [SMILES: Cc1ccc(-n2c(-c3ccc4c(c3)OCO4)cc3c2cc(-c2ccc4c(c2)OCO4)n3-c2ccc(C)cc2)cc1]

Colorless solid. Yield 137 mg (13%).[b] $R_f$=0.66 (SiO$_2$, AcOEt/hexanes, 1:2). Mp 236-237° C. (AcOEt). $^1$H NMR (500 MHz, C$_6$D$_6$) δ 7.23 (AA'XX', 4H), 6.92 (d, J=1.7 Hz, 2H), 6.87 (AA'XX', 4H), 6.81 (dd, J=8.1, 1.7 Hz, 2H), 6.56 (d, J=8.1 Hz, 2H), 6.43 (s, 2H), 5.23 (s, 4H), 2.02 (s, 6H). $^{13}$C NMR (125 MHz, C$_6$D$_6$) δ 148.0, 146.6, 138.4, 135.7, 135.2, 132.1, 130.0, 128.9, 125.5, 122.3, 109.2, 108.5, 100.9, 95.1, 20.8. HRMS (EI) calcd for $C_{34}H_{26}N_2O_4$: 526.1879 [M+]. found: 526.1882. Anal. calcd for $C_{34}H_{26}N_2O_4$: C, 77.55; H, 4.98; N, 5.32. found: C, 77.56; H, 4.94; N, 5.35. $\lambda_{abs}$ (toluene, ε×10$^{-3}$) 304 (23), 354 (37) nm.

EXAMPLE 12

1,4-bis(4-chlorophenyl)-2,5-bis(4-cyanophenyl)-1,4-dihydropyrrolo[3,2-b]pyrrole (11)

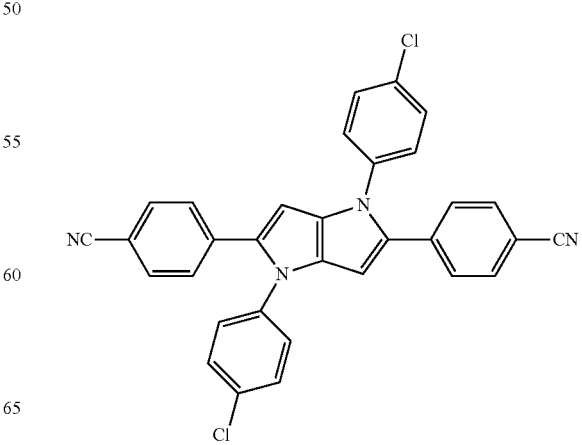

Yellow solid. Yield 33 mg (6%).[b] $R_f$=0.65 (SiO$_2$, AcOEt/hexanes, 1:2). Mp 324-325° C. (CH$_3$CO$_2$H). $^1$H NMR (500 MHz, CDCl$_3$) δ 7.52 (AA'XX', 4H), 7.40 (AA'XX', 4H), 7.28 (AA'XX', 4H), 7.20 (AA'XX', 4H), 6.47 (s, 2H). $^{13}$C NMR (125 MHz, CDCl$_3$) δ 137.7, 137.1, 135.2, 133.1, 132.4, 132.2, 129.8, 128.0, 126.4, 118.8, 109.7, 96.5. HRMS (EI) calcd for C$_{32}$H$_{18}$Cl$_2$N$_4$: 528.0905 [M$^+$]. found: 528.0905. Anal. calcd for C$_{32}$H$_{18}$Cl$_2$N$_4$: C, 72.60; H, 3.43; Cl, 13.39; N, 10.58. found: C, 72.50; H, 3.45; Cl, 13.37; N, 10.52. $\lambda_{abs}$ (CHCl$_3$, ε×10$^{-3}$) 399 (49) nm.

EXAMPLE 13

2,5-bis(4-fluorophenyl)-1,4-bis(4-methoxyphenyl)-1,4-dihydropyrrolo[3,2-b]pyrrole (12)

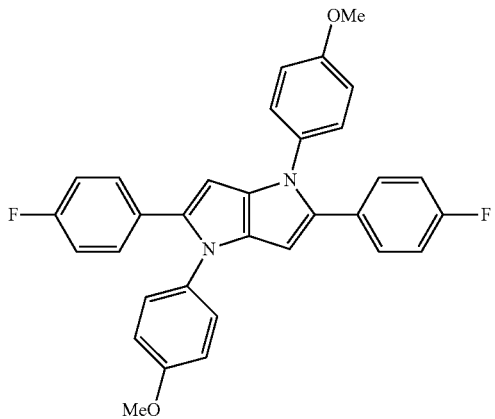 [SMILES: COc1ccc(-n2c(-c3ccc(F)cc3)cc3c2cc(-c2ccc(F)cc2)n3-c2ccc(OC)cc2)cc1]

Colorless solid. Yield 51 mg (7%).[b] $R_f$=0.86 (SiO$_2$, AcOEt/hexanes, 1:2). Mp 261-263° C. (CH$_3$CO$_2$H). $^1$H NMR (500 MHz, C$_6$D$_6$) δ 7.15 (AA'XX', 4H), 7.13 (AA'XX', 4H), 6.71 (AA'XX', 4H), 6.66 (AA'XX', 4H), 6.39 (s, 2H), 3.23 (s, 6H). $^{13}$C NMR (125 MHz, C$_6$D$_6$) δ 162.8, 160.9, 158.2, 135.1, 133.6, 132.6, 130.7, 130.6, 130.1, 130.0, 127.0, 115.5, 115.3, 114.7, 94.6, 54.9. HRMS (EI) calcd for C$_{32}$H$_{24}$F$_2$N$_2$O$_2$: 506.1806 [M$^+$]. found: 506.1815. Anal. calcd for C$_{32}$H$_{24}$F$_2$N$_2$O$_2$: C, 75.88; H, 4.78; F, 7.50; N, 5.53. found: C, 76.04; H, 4.79; F, 7.53; N, 5.48. $\lambda_{abs}$ (toluene, ε×10$^{-3}$) 345 (34) nm.

EXAMPLE 14

1,4-bis(4-nitrophenyl)-2,5-bis(4-methylphenyl)-1,4-dihydropyrrolo[3,2-b]pyrrole (13)

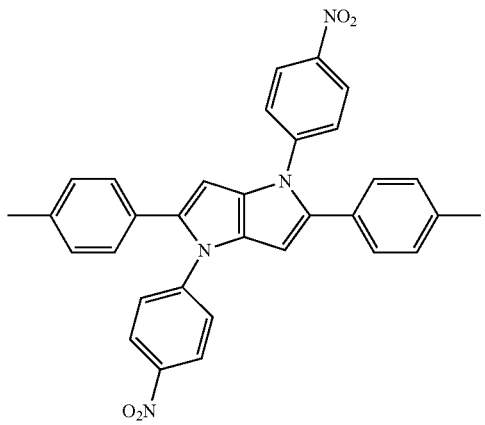

Red solid. Yield 55 mg (11%).[b] $R_f$=0.50 (SiO$_2$, AcOEt/hexanes, 1:2). Mp 317-319° C. (CH$_3$CO$_2$H). $^1$H NMR (500 MHz, DMSO) δ 8.28 (AA'XX', 4H), 7.50 (AA'XX', 4H), 7.13-7.17 (m, 8H), 6.69 (s, 2H), 2.30 (s, 6H). HRMS (EI) calcd for C$_{32}$H$_{24}$N$_4$O$_4$: 528.1790 [M$^+$]. found: 528.1798. Anal. calcd for C$_{32}$H$_{24}$N$_4$O$_4$: C, 72.72; H, 4.58; N, 10.60. found: C, 72.63; H, 4.44; N, 10.57. $\lambda_{abs}$ (CHCl$_3$, ε×10$^{-3}$) 360 (41) nm.

EXAMPLE 15

2,5-bis(3-nitrophenyl)-1,4-bis(4-octylphenyl)-1,4-dihydropyrrolo[3,2-b]pyrrole (14)

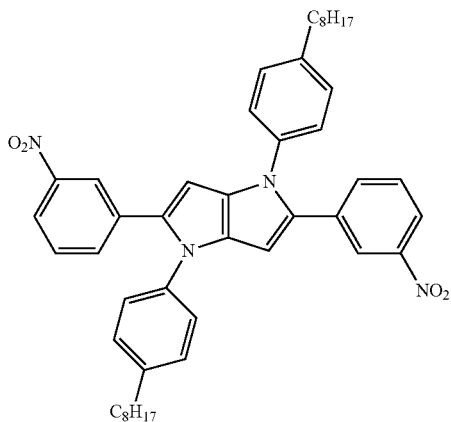

The resulting orange solid was filtered off and washed with cooled glacial acetic acid. Column chromatography (AcOEt/hexanes, 1:2) and crystallization from AcOEt gave pure product (84 mg, 12%)[b]. $R_f$=0.77 (SiO$_2$, AcOEt/hexanes, 1:9). Mp 193-194° C. (AcOEt). $^1$H NMR (500 MHz, CDCl$_3$) δ 8.14 (m, 2H), 7.97 (ddd, J=8.1, 2.3, 1.0 Hz, 2H), 7.42 (ddd, J=7.8, 1.7, 1.1 Hz, 2H), 7.33 (m, 2H), 7.22 (AA'XX', 4H), 7.18 (AA'XX', 4H), 6.50 (s, 2H), 2.69-2.60 (m, 4H), 1.70-1.59 (m, 4H), 1.40-1.20 (m, 20H), 0.89 (t, J=7.0 Hz, 6H). $^{13}$C NMR (125 MHz, CDCl$_3$) δ 148.3, 141.6, 136.7, 135.1, 134.1, 133.4, 132.7, 129.5, 128.9, 125.3, 122.2, 120.6, 95.4, 35.5, 31.9, 31.3, 29.4, 29.3, 29.2, 22.7, 14.1. HRMS (EI) calcd for C$_{46}$H$_{52}$N$_4$O$_4$: 724.3989 [M$^+$]. found: 724.3987. Anal. calcd for C$_{46}$H$_{52}$N$_4$O$_4$: C, 76.21; H, 7.23; N, 7.73. found: C, 76.21; H, 7.12; N, 7.74. $\lambda_{abs}$ (CHCl$_3$, ε×10$^{-3}$) 361 (39) nm.

EXAMPLE 16

2,5-di(pyridin-3-yl)-1,4-bis(4-methylphenyl)-1,4-dihydropyrrolo[3,2-b]pyrrole (15)

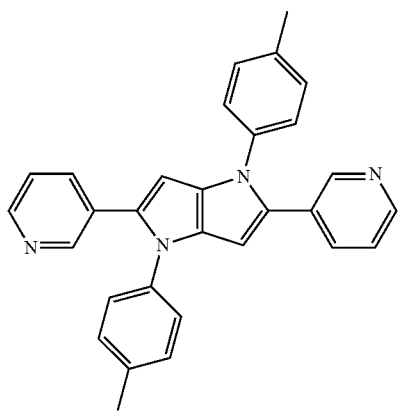 [SMILES: Cc1ccc(-n2c(-c3cccnc3)cc3c2cc(-c2cccnc2)n3-c2ccc(C)cc2)cc1]

Product didn't precipitate from reaction mixture. Acid was evaporated and residue was dissolved in Na$_2$CO$_{3(aq)}$ and extracted three times with dichloromethane (30 ml). Organic layers were combined, dried over Na$_2$SO$_4$ and concentrated under reduced pressure. The residual oil was purified by flash column chromatography (SiO$_2$, CH$_2$Cl$_2$/MeOH, 95:5). Beige solid. Yield 10 mg (1%).[b] R$_f$=0.41 (SiO$_2$, CH$_2$Cl$_2$/MeOH, 95:5). Mp. 216° C. (AcOEt, decomp.) $^1$H NMR (500 MHz, CDCl$_3$) δ 8.55 (d, J=1.6 Hz, 2H), 8.37-8.40 (m, 2H), 7.45-7.48 (m, 2H), 7.14-7.23 (m, 10H), 6.43 (s, 2H), 2.39 (s, 6H). $^{13}$C NMR (125 MHz, CDCl$_3$) δ 147.8, 146.0, 136.6, 136.5, 135.5, 132.7, 132.5, 130.1, 130.0, 125.3, 123.2, 95.1, 21.0. LRMS (API) calcd for C$_{30}$H$_{24}$N$_4$: 441.2 [M+H$^+$]. found: 441.5. λ$_{abs}$ (CHCl$_3$, ε×10$^{-3}$) 361 (47) nm.

In examples 17-27 the syntheses of compounds 16-26 have been described.

EXAMPLE 17

1,4-bis(4-methylphenyl)-2,5-bis(4-((trimethylsilyl)ethynyl)phenyl)-1,4-dihydropyrrolo[3,2-b]pyrrole (16)

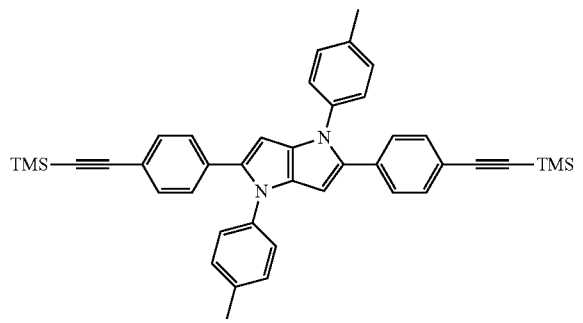 [SMILES: Cc1ccc(-n2c(-c3ccc(C#C[Si](C)(C)C)cc3)cc3c2cc(-c2ccc(C#C[Si](C)(C)C)cc2)n3-c2ccc(C)cc2)cc1]

Yellow solid. Yield 567 mg (15%).[b] R$_f$=0.78 (SiO$_2$, hexanes/CH$_2$Cl$_2$, 1:1). Mp 314-315° C. (toluene, decomp.). $^1$H NMR (500 MHz, CDCl$_3$) δ 7.26 (AA'XX', 4H), 7.14 (m, 12H), 6.36 (s, 2H), 2.37 (s, 6H), 0.23 (s, 18H); $^{13}$C NMR (125 MHz, CDCl$_3$) δ 137.5, 135.9, 130.0, 125.3, 21.2. HRMS (EI) calcd for C$_{42}$H$_{42}$N$_2$Si$_2$: 630.2905[M$^+$]. found: 630.2905. λ$_{abs}$ (CH$_2$Cl$_2$, ε×10$^{-3}$) 393 (60) nm.

EXAMPLE 18

2,5-bis(2-bromophenyl)-1,4-bis(4-methylphenyl)-1,4-dihydropyrrolo[3,2-b]pyrrole (17)

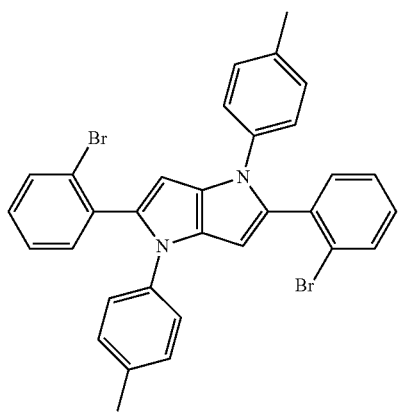 [SMILES: Cc1ccc(-n2c(-c3ccccc3Br)cc3c2cc(-c2ccccc2Br)n3-c2ccc(C)cc2)cc1]

Yellowish solid. Yield 291 mg (49%).[c] R$_f$=0.68 (SiO$_2$, AcOEt/hexanes, 1:4). Mp 239-241° C. (AcOEt). $^1$H NMR (500 MHz, CDCl$_3$) δ 7.57 (dd, J=8.1, 1.1 Hz, 2H), 7.28 (dd, J=7.6, 1.7 Hz, 2H), 7.20 (dt, J=7.5, 1.1 Hz, 2H), 7.10 (m, 10H), 6.45 (s, 2H), 2.31 (s, 6H). $^{13}$C NMR (125 MHz, CDCl$_3$) δ 137.4, 135.1, 134.7, 133.4, 133.1, 133.0, 129.8, 129.5, 128.6, 126.9, 124.4, 124.0, 96.3, 20.9. HRMS (EI) calcd for C$_{32}$H$_{24}$N$_2$Br$_2$: 594.0306 [M$^+$]. found: 594.0305. Anal. calcd for C$_{32}$H$_{24}$Br$_2$N$_2$: C, 64.45; H, 4.06; Br, 26.80; N, 4.70. found: C, 64.51; H, 4.24; Br, 26.78; N, 4.52. λ$_{abs}$ (CH$_2$Cl$_2$, ε×10$^{-3}$) 306 (19) nm, 333 (18) nm.

EXAMPLE 19

2,5-bis(2-methoxyphenyl)-1,4-bis(4-methylphenyl)-1,4-dihydropyrrolo[3,2-b]pyrrole (18)

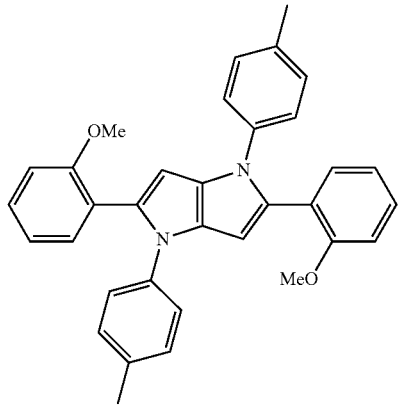 [SMILES: COc1ccccc1-c1cc2c(cc(-c3ccccc3OC)n2-c2ccc(C)cc2)n1-c1ccc(C)cc1]

Beige solid. Yield 224 mg (45%).[c] R$_f$=0.61 (SiO$_2$, AcOEt/hexanes, 1:4). Mp 286-289° C. (AcOEt). $^1$H NMR (500 MHz, CDCl$_3$) δ 7.31 (dd, J=7.4, 1.3 Hz, 2H), 7.23 (dt, J=8.8, 1.4 Hz, 2H), 7.13 (d, J=8.2 Hz, 4H), 7.06 (d, J=8.2 Hz, 4H), 6.92 (t, J=7.4 Hz, 2H), 6.75 (d, J=8.2 Hz, 2H), 6.37 (s, 2H), 3.37 (s, 6H), 2.31 (s, 6H). $^{13}$C NMR (125 MHz, CDCl$_3$) δ 156.8, 138.6, 134.1, 131.8, 131.6, 130.0, 129.1, 128.4, 123.7, 123.4, 120.5, 111.0, 95.0, 54.9, 20.9. HRMS (EI) calcd for C$_{34}$H$_{30}$N$_2$O$_2$: 498.2307 [M$^+$]. found: 498.2309. Anal. calcd for C$_{34}$H$_{30}$N$_2$O$_2$: C, 81.90; H, 6.06; N, 5.62. found: C, 81.62; H, 6.28; N, 5.39. λ$_{abs}$ (CH$_2$Cl$_2$, ε×10$^{-3}$) 309 (23) nm, 338 (27) nm.

EXAMPLE 20

2,5-bis(2-(allyloxy)phenyl)-1,4-bis(4-methylphenyl)-1,4-dihydropyrrolo[3,2-b]pyrrole (19)

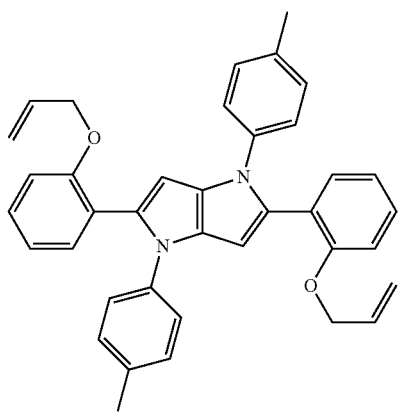 [SMILES: C=CCOc1ccccc1-c1cc2c(cc(-c3ccccc3OCC=C)n2-c2ccc(C)cc2)n1-c1ccc(C)cc1]

Beige solid. Yield 248 mg (45%).[c] R$_f$=0.65 (SiO$_2$, AcOEt/hexanes, 1:4). Mp 203-204° C. (AcOEt). $^1$H NMR (500 MHz, CDCl$_3$) δ 7.34 (dd, J=7.5, 1.7 Hz, 2H), 7.20 (dt, J=7.5, 1.7 Hz, 2H), 7.14 (d, J=8.2 Hz, 4H), 7.05 (d, J=8.2 Hz, 4H), 6.92 (dt, J=7.4, 0.6 Hz, 2H), 6.76 (d, J=8.2 Hz, 2H), 6.38 (s, 2H), 5.60 (m, 2H), 5.07 (m, 2H), 4.18 (m, 2H), 2.31 (s, 6H). $^{13}$C NMR (125 MHz, CDCl$_3$) δ 155.8, 138.7, 134.1, 133.8, 131.8, 130.1, 129.2, 128.3, 124.0, 123.3, 120.6, 116.8, 112.5 95.4, 68.9, 20.9. HRMS (EI) calcd for C$_{38}$H$_{34}$N$_2$O$_2$: 550.2620 [M$^+$]. found: 550.2635. Anal. calcd for C$_{38}$H$_{34}$N$_2$O$_2$: C, 82.88; H, 6.22; N, 5.09. found: C, 83.05; H, 6.32; N, 5.09. λ$_{abs}$ (CH$_2$Cl$_2$, ε×10$^{-3}$) 308 (24) nm, 336 (28) nm.

EXAMPLE 21

1,4-bis(4-methylphenyl)-2,5-bis(4-(pentafluoro-λ$^6$-sulfanyl)phenyl)-1,4-dihydropyrrolo[3,2-b]pyrrole (20)

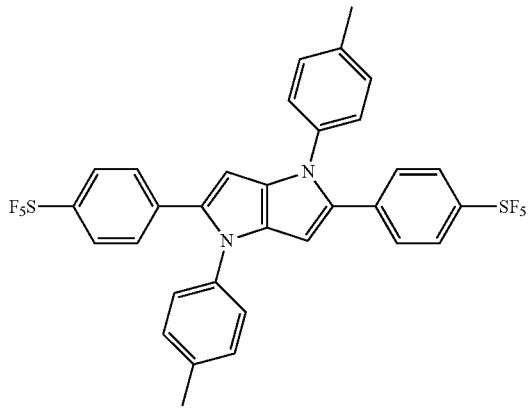

Yellowish solid. Yield 241 mg (35%).[c] R$_f$=0.70 (SiO$_2$, AcOEt/hexanes, 1:4). Mp 322-324° C. (AcOEt, decomp.). $^1$H NMR (500 MHz, CDCl$_3$) δ 7.57 (d, J=8.8 Hz, 4H), 7.23 (m, 8H), 7.16 (d, J=8.2 Hz, 4H), 6.43 (s, 2H), 2.41 (s, 6H). $^{13}$C NMR (125 MHz, CDCl$_3$) δ 136.9, 136.7, 136.4, 134.6, 133.0, 130.1, 127.3, 125.8, 125.2, 95.6, 21.0. HRMS (EI) calcd for C$_{32}$H$_{24}$F$_{10}$N$_2$S$_2$: 690.1221 [M$^+$]. found: 690.1230. Anal. calcd for C$_{32}$H$_{24}$F$_{10}$N$_2$S$_2$: C, 55.65; H, 3.50; F, 27.51; N, 4.06; S, 9.29. found: C, 55.64; H, 3.50; N, 4.12; F, 27.41; S, 9.18. λ$_{abs}$ (CH$_2$Cl$_2$, ε×10$^{-3}$) 381 (41) nm.

EXAMPLE 22

1,2,4,5-tetrakis(4-(pentafluoro-λ$^6$-sulfanyl)phenyl)-1,4-dihydropyrrolo[3,2-b]pyrrole (21)

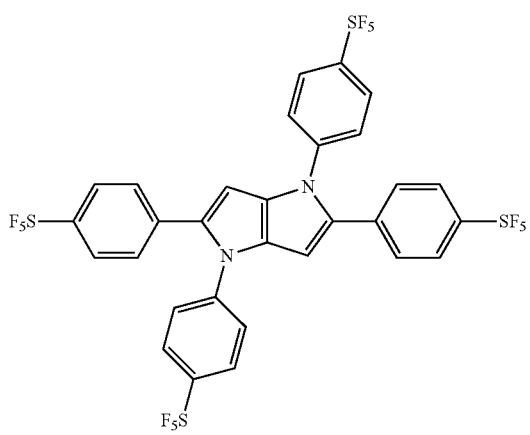

Yellowish solid. Yield 238 mg (26%).[c] R$_f$=0.67 (SiO$_2$, AcOEt/hexanes, 1:4). Mp 329-331° C. (AcOEt). $^1$H NMR (500 MHz, CDCl$_3$) δ 7.83 (d, J=8.2 Hz, 4H), 7.68 (d, J=8.2 Hz, 4H), 7.34 (d, J=8.1 Hz, 4H), 7.28 (d, J=8.1 Hz, 4H) 6.54 (s, 2H); $^{13}$C NMR (125 MHz, CDCl$_3$) δ 151.2, 141.7, 135.7, 134.8, 132.5, 127.7, 127.6, 126.4, 124.6, 97.9. HRMS (EI) calcd for C$_{30}$H$_{18}$F$_{20}$N$_2$S$_4$: 914.0034 [M$^+$]. found: 914.0029. Anal. calcd for C$_{30}$H$_{18}$F$_{20}$N$_2$S$_4$: C, 39.39; H, 1.98; F, 41.54; N, 3.06; S, 14.02. found: C, 39.57; H, 2.06; F, 41.32; N, 3.09; S, 14.18. λ$_{abs}$ (CH$_2$Cl$_2$, ε×10$^{-3}$) 319 (23) nm, 376 (42) nm.

EXAMPLE 23

1,4-bis(4-bromophenyl)-2,5-bis(4-cyanophenyl)-1,4-dihydropyrrolo[3,2-b]pyrrole (22)

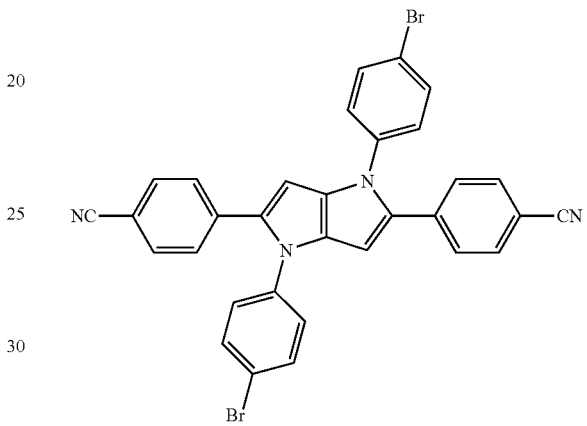

Yellow solid. Yield 142 mg (23%).[c] R$_f$=0.56 (SiO$_2$, AcOEt/hexanes, 1:4). Mp 351-353° C. (AcOEt, decomp.). $^1$H NMR (500 MHz, CDCl$_3$,) δ 7.55 (dd, J=6.8, 1.9 Hz, 4H), 7.52 (dd, J=6.8, 1.9 Hz, 4H), 7.27 (dd, J=6.9, 2.0 Hz, 4H), 7.13 (dd, J=6.9, 2.0 Hz, 4H) 6.54 (s, 2H) $^{13}$C NMR (125 MHz, CDCl$_3$) δ 138.2, 137.1, 135.2, 133.1, 132.8, 132.2, 128.0, 126.8, 120.3, 118.9, 109.8, 96.6. HRMS (EI) calcd for C$_{32}$H$_{18}$N$_4$Br$_2$: 615.9898 [M$^+$]. found: 615.9924. Anal. calcd for C$_{32}$H$_{18}$Br$_2$N$_4$: C, 62.16; H, 2.93; Br, 25.85; N, 9.06. found: C, 62.11; H, 3.03; Br, 25.94; N, 9.15. λ$_{abs}$ (CH$_2$Cl$_2$, ε×10$^{-3}$) 399 (50) nm.

EXAMPLE 24

2,5-bis(4-bromo-2-nitrophenyl)-1,4-bis(4-hexylphenyl)-1,4-dihydropyrrolo[3,2-b]pyrrole (23)

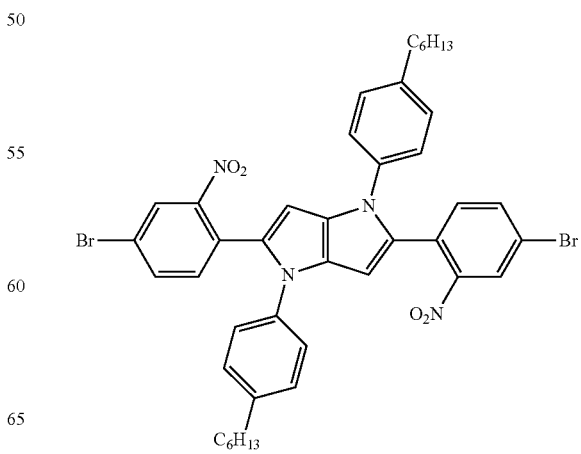

Purple solid. Yield 208 mg (25%).[b] $R_f$=0.75 (SiO$_2$, CH$_2$Cl$_2$/hexanes, 1:1). $^1$H NMR (500 MHz, CDCl$_3$) δ 7.86 (d, J=2.0 Hz, 2H), 7.59 (dd, J=8.3, 2.0 Hz, 2H), 7.28 (s, 2H), 7.11 (AA'XX', 4H), 7.07 (AA'XX', 4H), 6.32 (s, 2H), 2.66-2.52 (m, 4H), 1.60 (quin, J=14.5 Hz, 4H), 1.31 (s, 12H), 0.89 (t, J=6.8 Hz, 6H). $^{13}$C NMR (125 MHz, CDCl$_3$) δ 149.2, 141.3, 136.1, 135.3, 134.2, 132.0, 129.9, 129.5, 127.3, 127.3, 124.7, 121.0, 95.7, 35.6, 31.8, 31.4, 29.0, 22.8, 14.2. HRMS (EI) calcd for C$_{42}$H$_{42}$Br$_2$N$_4$O$_4$: 824.1588 [M$^+$]. found: 824.1589. Anal. calcd for C$_{42}$H$_{42}$Br$_2$N$_4$O$_4$: C, 61.03; H, 5.12; N, 6.78; Br, 19.33. found: C, 60.94; H, 5.20; N, 6.69; Br, 19.29.

EXAMPLE 25

2,5-bis(benzo[b]thiophen-2-yl)-1,4-bis(4-methylphenyl)-1,4-dihydropyrrolo[3,2-b]pyrrole (24)

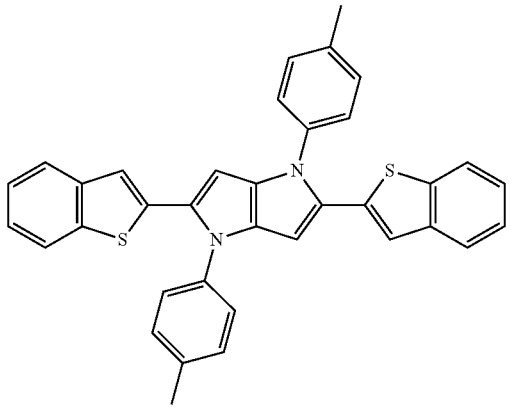 [SMILES: Cc1ccc(-n2c(-c3cc4ccccc4s3)cc3c2cc(-c2cc4ccccc4s2)n3-c2ccc(C)cc2)cc1]

Purple solid. Yield 20 mg (4%).[b] $R_f$=0.72 (SiO$_2$, AcOEt/hexanes, 4:6). $^1$H NMR (500 MHz, CDCl$_3$) δ 7.69 (d, J=7.8, 2H), 7.54 (d, J=7.2 Hz, 2H), 7.34 (AA'XX', 4H), 7.26 (AA'XX', 4H), 7.23 (dd, J=4.4, 1.5 Hz; 2H), 7.21 (dd, J=7.1, 1.0 Hz, 2H), 6.77 (s, 2H), 6.45 (s, 2H), 2.44 (s, 6H). $^{13}$C NMR (125 MHz, CDCl$_3$) 3140.3, 139.0, 136.9, 136.8, 135.8, 132.8, 130.2, 130.2, 130.0, 126.1, 124.2, 123.7, 123.1, 121.8, 120.2, 95.0, 21.2. HRMS (EI) calcd for C$_{36}$H$_{26}$N$_2$S$_2$: 550.1537 [M$^+$]. found: 550.1551.

EXAMPLE 26

2,5-di(benzofuran-2-yl)-1,4-bis(4-methylphenyl)-1,4-dihydropyrrolo[3,2-b]pyrrole (25)

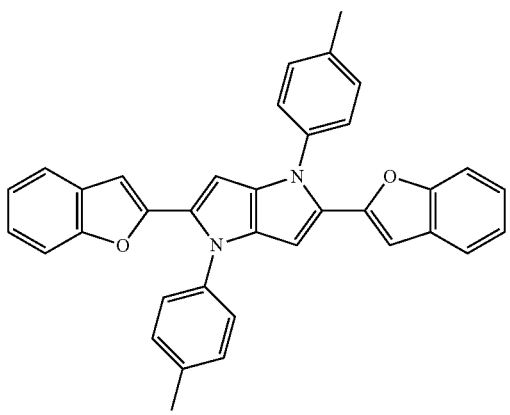 [SMILES: Cc1ccc(-n2c(-c3cc4ccccc4o3)cc3c2cc(-c2cc4ccccc4o2)n3-c2ccc(C)cc2)cc1]

Orange solid. Yield 78 mg (15%).[b] $^1$H NMR (500 MHz, CDCl$_3$) δ 7.41 (AA'XX', 4H), 7.36 (m, 4H), 7.32 (AA'XX', 4H), 7.18 (m, 2H), 7.13 (dd, J=7.6, 1.0 Hz, 2H), 6.68 (s, 2H), 5.96 (s, 2H), 2.49 (s, 6H). $^{13}$C NMR (125 MHz, CDCl$_3$) δ 153.9, 149.8, 137.4, 136.9, 133.5, 130.0, 129.2, 128.0, 126.4, 123.6, 122.7, 120.3, 110.6, 101.0, 93.7, 21.2. HRMS (ESI) calcd for C$_{36}$H$_{26}$N$_2$O$_2$: 518.1992 [M$^+$]. found: 518.1992.

EXAMPLE 27

1,4-bis(4-methylphenyl)-2,5-bis(thiazol-2-yl)-1,4-dihydropyrrolo[3,2-b]pyrrole (26)

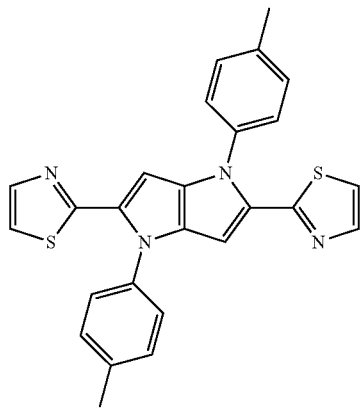 [SMILES: Cc1ccc(-n2c(-c3nccs3)cc3c2cc(-c2nccs2)n3-c2ccc(C)cc2)cc1]

Yellow solid. Yield 45 mg (10%).[b] $^1$H NMR (500 MHz, CDCl$_3$) δ 7.67 (d, J=3.3 Hz, 2H), 7.31 (AA'XX', 4H), 7.27 (AA'XX', 4H), 7.08 (d, J=3.3 Hz, 2H), 6.77 (s, 2H), 2.44 (s, 6H). $^{13}$C NMR (125 MHz, CDCl$_3$) δ 160.0, 142.6, 137.8, 136.2, 133.8, 130.1, 127.0, 117.6, 95.8, 21.4. HRMS (ESI) calcd for C$_{26}$H$_{20}$N$_4$S$_2$: 452.1139 [M$^+$]. found: 452.1129.

EXAMPLE 28

General procedure for the synthesis of arylated 1,4-dihydropyrrolo[3,2-b]pyrroles (27-34)

Parent 1,4-dihydropyrrolo[3,2-b]pyrrole (0.25 mmol), aryl bromide (1 mmol), KOAc (1 mmol) and PdCl(C$_3$H$_5$)(dppb) (0.01 mmol) were placed in a 25 ml Schlenk flask, which was flushed with Argon prior to use. Then 8 ml of dry DMA was added and resulting mixture was stirred at 150° C. for 3 days. Product was purified by means of flash column chromatography, and then recrystallized from toluene or ethyl acetate. Obtained crystals were dried under reduced pressure.

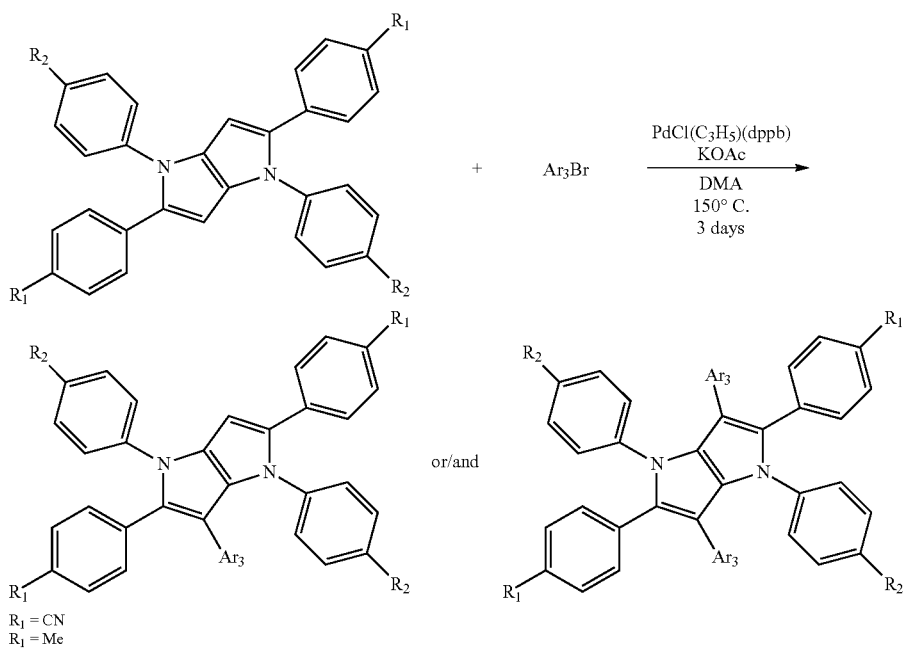

R₁ = CN
R₁ = Me

The examples 29-36 present synthetic results of applied procedure—compounds 27-34.

EXAMPLE 29

2,5-bis(4-cyanophenyl)-3-(9,9-dioctyl-9H-fluoren-3-yl)-1,4-bis(4-methylphenyl)-dihydropyrrolo[3,2-b]pyrrole (27)

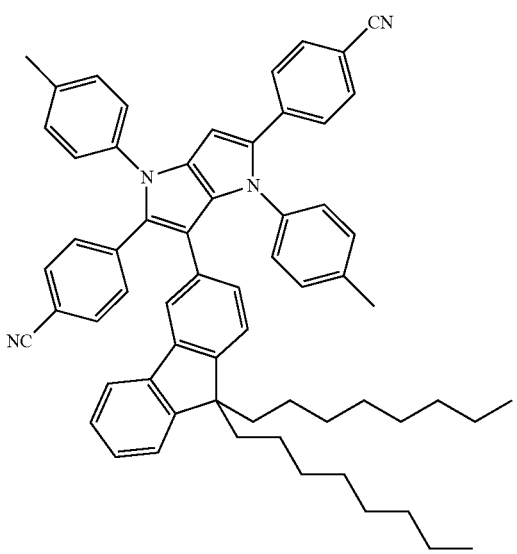 [SMILES: CCCCCCCCC1(CCCCCCCC)c2ccccc2-c2cc(-c3c(-c4ccc(C#N)cc4)n(-c4ccc(C)cc4)c4cc(-c5ccc(C#N)cc5)n(-c5ccc(C)cc5)c34)ccc21]

Yellow solid. Product was purified by means of flash column chromatography (SiO₂, CH₂Cl₂/hexanes 1:1). Yield 66 mg (30%). $R_f$=0.66 (SiO₂, AcOEt/hexanes, 1:4). Mp 228-231° C. (toluene). ¹H NMR (500 MHz, CDCl₃) δ 7.62 (d, J=7.2 Hz 1H), 7.42 (AA'XX', 2H), 7.33 (m, 1H), 7.29 (m, 3H), 7.27 (m, 1H), 7.21 (m, 5H), 7.12 (AA'XX', 2H), 7.07 (d, J=8.4 Hz, 2H), 6.86 (s, 1H), 6.79 (s, 4H), 6.64 (dd, J=7.7, 1.3 Hz, 1H), 6.54 (s, 1H), 2.40 (s, 3H), 2.25 (s, 3H), 1.80 (m, 2H), 1.63 (m, 2H), 1.21 (m, 4H), 1.15 (m, 8H), 1.04 (m, 4H), 0.99 (m, 4H), 0.82 (t, J=7.0 Hz, 6H), 0.49 (quin, J=7.8 Hz, 4H). ¹³C NMR (125 MHz, CDCl₃) δ 150.7, 150.2, 140.9, 139.4, 137.8, 136.9, 136.2, 135.6, 131.9, 131.3, 130.8, 130.0, 129.2, 127.9, 127.1, 125.3, 122.8, 119.4, 118.6, 112.3, 109.0, 94.1, 54.8, 40.3, 31.8, 30.0, 29.5, 29.3, 23.7, 22.6, 21.0, 14.1. HRMS (ESI) calcd for C₆₃H₆₄N₄: 876.5131 [M⁺]. found: 876.5124. Anal. calcd for C₆₃H₆₄N₄: C, 86.26; H, 7.35; N, 6.39. found: C, 86.02; H, 7.38; N, 6.30. $\lambda_{abs}$ (CH₂Cl₂, ε×10⁻³) 404 (40) nm.

EXAMPLE 30

2,5-bis(4-cyanophenyl)-1,4-bis(4-methylphenyl)-3-(4-nitrophenyl)-dihydropyrrolo[3,2-b]pyrrole (28)

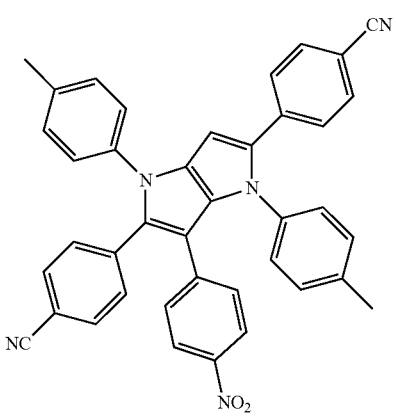 [SMILES: Cc1ccc(-n2c(-c3ccc(C#N)cc3)c(-c3ccc([N+](=O)[O-])cc3)c3c2cc(-c2ccc(C#N)cc2)n3-c2ccc(C)cc2)cc1]

Orange solid. Product was purified by means of flash column chromatography (SiO₂, CH₂Cl₂/hexanes 1:1). Yield 36 mg (24%). $R_f$=0.51 (SiO₂, AcOEt/hexanes, 1:4). Mp 344-346° C. (toluene). ¹H NMR (500 MHz, CDCl₃) δ 7.80 (AA'XX', 2H), 7.44 (AA'XX', 2H), 7.39 (AA'XX', 2H), 7.20 (t, J=8.5 Hz, 4H), 7.08 (AA'XX', 2H), 7.03 (AA'XX', 2H), 6.95 (d, J=8.0 Hz, 2H), 6.84-6.81 (m, 2H), 6.51 (s, 1H), 2.40 (s, 3H), 2.34 (s, 3H). ¹³C NMR (125 MHz, CDCl₃) δ 145.8, 140.4, 138.0, 137.4, 136.9, 136.2, 136.1, 136.0, 135.9, 132.0, 131.9, 131.8, 131.1, 130.7, 130.1, 129.6, 128.0, 127.5, 125.5, 124.8, 122.7, 119.0, 118.6, 110.3, 109.4, 109.0, 94.5, 21.1, 21.0. HRMS (EI) calcd for $C_4H_{27}N_5O_2$: 609.2165 [M+]. found: 609.2184. $\lambda_{abs}$ (CH$_2$Cl$_2$, $\varepsilon \times 10^{-3}$) 393 (40) nm.

EXAMPLE 31

2,5-bis(4-cyanophenyl)-1,4-bis(4-methylphenyl)-3,6-bis-(4-nitrophenyl)-dihydropyrrolo[3,2-b]pyrrole (29)

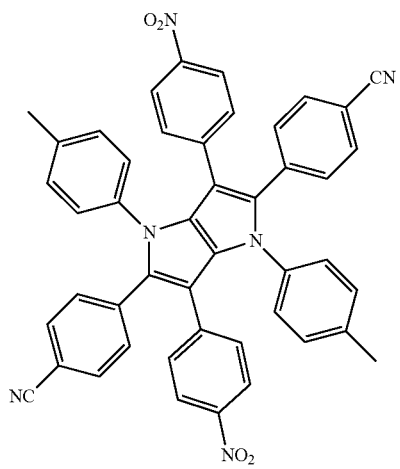 [SMILES: Cc1ccc(-n2c(-c3ccc(C#N)cc3)c(-c3ccc([N+](=O)[O-])cc3)c3c2c(-c2ccc([N+](=O)[O-])cc2)c(-c2ccc(C#N)cc2)n3-c2ccc(C)cc2)cc1]

Orange solid. Product was purified by means of flash column chromatography (SiO$_2$, CH$_2$Cl$_2$/hexanes 2:1) Yield 97 mg (53%). R$_f$=0.42 (SiO$_2$, AcOEt/hexanes, 1:4). $^1$H NMR (500 MHz, CDCl$_3$) δ 7.79 (d, 4H), 7.35 (d, 4H), 6.98 (d, 4H), 6.91 (d, 4H), 6.82 (d, 4H), 6.77 (d, 4H), 2.32 (s, 6H). $^{13}$C NMR (125 MHz, CDCl$_3$) δ 145.8, 140.0, 138.2, 135.8, 135.2, 133.3, 131.8, 131.4, 131.0, 129.5, 129.2, 127.6, 124.8, 122.8, 118.5, 110.6, 108.0, 21.1. HRMS (EI) calcd for $C_{46}H_{30}N_6O_4$ [M+]=730.2329. found [M+]=730.2345. Anal. calcd for $C_{46}H_{30}N_6O_4$: C, 75.60; H, 4.14; N, 11.50 found: C, 75.56; H, 4.20; N, 11.41. $\lambda_{abs}$ (CH$_2$Cl$_2$, $\varepsilon \times 10^{-3}$) 381 (45) nm.

EXAMPLE 32

2,5-bis(4-cyanophenyl)-1,4-bis(4-methylphenyl)-3,6-bis(4-(pentafluoro-$\lambda^6$-sulfanyl)phenyl)-1,4-dihydropyrrolo[3,2-b]pyrrole (30)

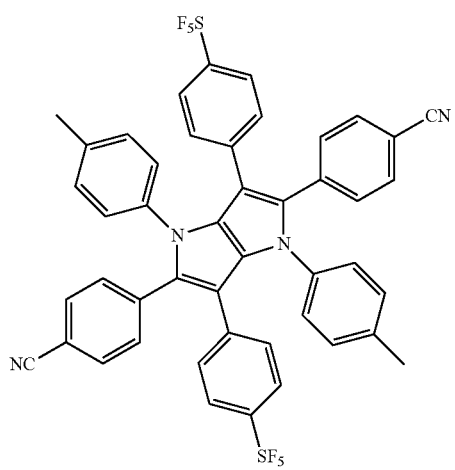

Yellow-greenish solid. Product was purified by means of flash column chromatography (SiO$_2$, CH$_2$Cl$_2$/hexanes 1:1-3:1). Yield 78 mg (35%). R$_f$=0.56 (SiO$_2$, AcOEt/hexanes, 1:4). $^1$H NMR (500 MHz, CDCl$_3$) δ 7.36 (AA'XX', 4H), 7.30 (AA'XX', 4H), 7.01 (AA'XX', 4H), 6.86 (d, J=8.0 Hz, 4H), 6.78 (d, J=8.5 Hz, 4H), 6.70 (AA'XX', 4H), 2.29 (s, 6H). $^{13}$C NMR (125 MHz, CDCl$_3$) δ 137.8, 136.7, 135.9, 135.2, 132.3, 131.8, 131.1, 130.4, 129.5, 129.4, 127.4, 125.2, 125.1, 118.7, 110.2, 108.0, 20.8. HRMS (EI) calcd for $C_{46}H_{30}N_4F_{10}S_2$: 892.1752 [M+]. found: 892.1734. $\lambda_{abs}$ (CH$_2$Cl$_2$, $\varepsilon \times 10^{-3}$) 395 (33) nm.

EXAMPLE 33

2,5-bis(4-cyanophenyl)-1,4-bis(4-methylphenyl)-3-(pyridin-3-yl)-1,4-dihydropyrrolo[3,2-b]pyrrole (31)

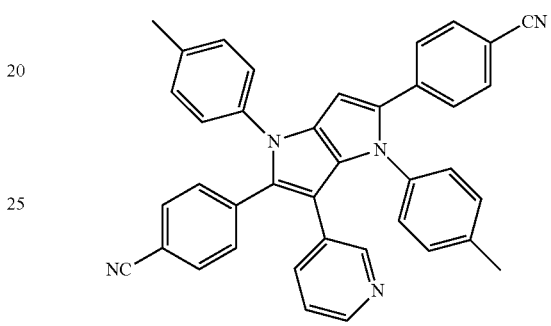

Yellow solid. Product was purified by means of flash column chromatography (SiO$_2$, CH$_2$Cl$_2$/MeOH 95:5). Yield 30 mg (21%). R$_f$=0.71 (SiO$_2$, CH$_2$Cl$_2$/MeOH, 95:5). Mp 319-320° C. (toluene, decomp.). $^1$H NMR (500 MHz, CDCl$_3$) δ 8.34 (d, J=2.0 Hz, 1H), 8.02 (s, 1H), 7.43 (d, J=7.8 Hz, 2H), 7.36 (d, J=7.8 Hz, 2H) 7.20 (m, 4H), 7.09 (d, J=7.6 Hz, 2H), 7.01 (m, 3H), 6.91 (m, 3H), 6.80 (d, J=7.5 Hz, 2H), 6.52 (s, 1H), 2.39 (s, 3H), 2.31 (s, 3H). $^{13}$C NMR (125 MHz, CDCl$_3$) δ 150.0, 147.0, 137.9, 137.6, 137.5, 136.6, 136.3, 136.2, 136.0, 135.6, 132.1, 131.9, 131.8, 131.7, 131.3, 131.0, 130.1, 129.6, 129.3, 127.9, 127.3, 125.4, 122.4, 119.0, 118.8, 109.9, 109.2, 107.2, 94.5, 21.1, 21.0. HRMS (EI) calcd for $C_{39}H_{27}N_5$: 565.2266 [M+]. found: 565.2280. $\lambda_{abs}$ (CH$_2$Cl$_2$, $\varepsilon \times 10^{-3}$) 395 (33) nm.

EXAMPLE 34

2,5-bis(4-cyanophenyl)-1,4-bis(4-methylphenyl)-3,6-di(pyridin-3-yl)-1,4-dihydropyrrolo[3,2-b]pyrrole (32)

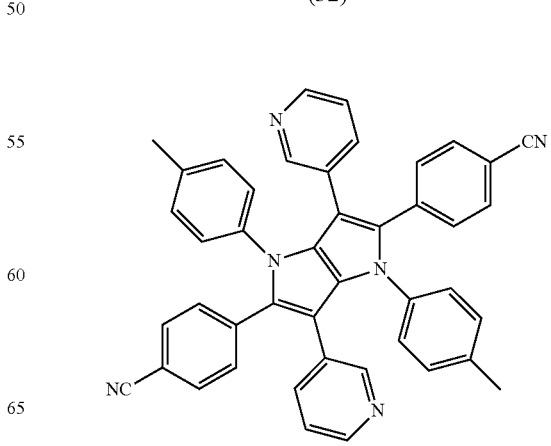

Yellow solid. Product was purified by means of flash column chromatography (SiO$_2$, CH$_2$Cl$_2$/MeOH 95:5). Yield 76 mg (47%). R$_f$=0.55 (SiO$_2$, CH$_2$Cl$_2$/MeOH, 95:5). Mp 345-347° C. (toluene, decomp.). $^1$H NMR (500 MHz, CDCl$_3$) δ 8.33 (d, J=3.0 Hz, 2H), 8.01 (s, 2H), 7.32 (d, J=8.2 Hz, 4H), 7.01 (d, J=7.6 Hz, 2H), 6.97 (d, J=8.2 Hz, 4H), 6.89 (m, 6H), 6.75 (d, J=8.0 Hz, 4H), 2.31 (s, 6H). $^{13}$C NMR (125 MHz, CDCl$_3$) δ 151.0, 147.0, 137.8, 137.6, 136.1, 135.1, 133.1, 131.7, 131.2, 129.5, 129.4, 129.2, 127.4, 122.5, 118.7, 110.1, 106.1, 21.1. HRMS (EI) calcd for C$_{44}$H$_{30}$N$_6$: 642.2532 [M+]. found: 642.2521. λ$_{abs}$ (CH$_2$Cl$_2$, ε×10$^{-3}$) 396 (36) nm.

EXAMPLE 35

2,3,5-tris(4-cyanophenyl)-1,4-bis(4-methylphenyl)-1,4-dihydropyrrolo[3,2-b]pyrrole (33)

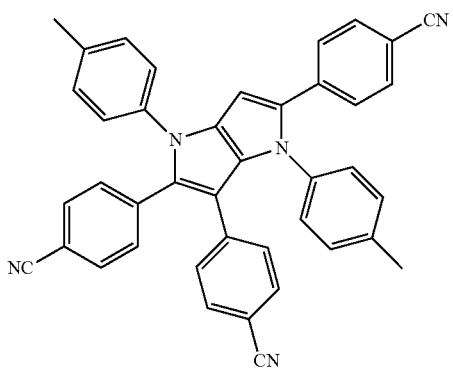 [SMILES: Cc1ccc(-n2c(-c3ccc(C#N)cc3)c(-c3ccc(C#N)cc3)c3c2cc(-c2ccc(C#N)cc2)n3-c2ccc(C)cc2)cc1]

Yellow solid. Product was purified by means of flash column chromatography (SiO$_2$, CH$_2$Cl$_2$/hexanes 1:1-3:1). Yield 71 mg (48%). R$_f$=0.41 (SiO$_2$, AcOEt/hexanes, 1:4). Mp 325-326° C. (toluene). $^1$H NMR (500 MHz, CDCl$_3$) δ 7.43 (d, J=8.2 Hz, 2H), 7.38 (d, J=8.2 Hz, 2H), 7.20 (m, 6H), 7.07 (d, J=8.1 Hz, 2H), 7.00 (d, J=8.2 Hz, 2H), 6.94 (d, J=7.9 Hz, 2H), 6.79 (m, 4H), 2.39 (s, 3H), 2.36 (s, 3H). $^{13}$C NMR (125 MHz, CDCl$_3$) δ 138.3, 137.8, 136.8, 136.3, 136.1, 136.0, 135.9, 131.9, 131.8, 131.7, 131.2, 131.1, 130.7, 130.1, 129.5, 128.0, 127.4, 125.4, 119.0, 118.7, 110.1, 109.5, 109.4, 109.3, 94.5, 21.1, 21.0. HRMS (EI) calcd for C$_{41}$H$_{27}$N$_5$: 589.2266 [M$^+$]. found: 589.2259. Anal. calcd for C$_{41}$H$_{27}$N$_5$: C, 83.51; H, 4.62; N, 11.88. found: C, 83.47; H, 4.63; N, 11.72. λ$_{abs}$ (CH$_2$Cl$_2$, ε×10$^{-3}$) 400 (43) nm.

EXAMPLE 36

2,5-bis(4-cyanophenyl)-3-(4-methoxyphenyl)-1,4-bis(4-methylphenyl)-1,4-dihydropyrrolo[3,2-b]pyrrole (34)

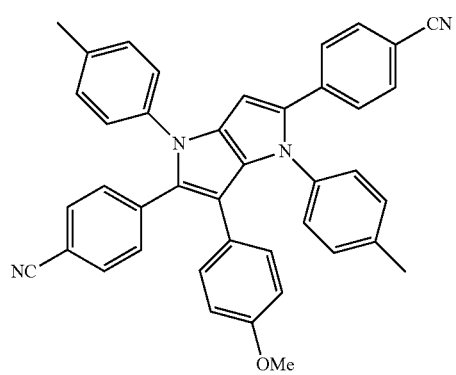

Yellow solid. Product was purified by means of flash column chromatography (SiO$_2$, AcOEt/hexanes 1:4). Yield 50 mg (34%). R$_f$=0.45 (SiO$_2$, AcOEt/hexanes, 1:4). Mp 298-300° C. (toluene). $^1$H NMR (500 MHz, CDCl$_3$) δ 7.42 (d, J=8.3 Hz, 2H), 7.33 (d, J=8.3 Hz, 2H), 7.20 (d, J=8.3 Hz, 2H), 7.17 (d, J=8.3 Hz, 2H), 7.08 (d, J=8.1 Hz, 2H), 7.03 (d, J=8.2 Hz, 2H), 6.89 (d, J=8.0 Hz, 2H), 6.78 (d, J=8.1 Hz, 2H), 6.62 (d, J=8.5 Hz, 2H), 6.52 (d, J=6.8 Hz, 2H), 6.51 (s, 1H), 3.75 (s, 3H), 2.39 (s, 3H), 2.32 (s, 3H). $^{13}$C NMR (125 MHz, CDCl$_3$) δ 158.1, 137.8, 137.1, 136.8, 136.7, 136.1, 135.8, 135.6, 131.9, 131.7, 131.7, 131.6, 131.4, 130.9, 130.0, 129.2, 127.9, 127.3, 125.3, 125.0, 113.1, 111.3, 109.1, 108.9, 94.6, 55.2, 21.1, 21.0. HRMS (EI) calcd for C$_{41}$H$_{30}$N$_4$O: 594.2420 [M$^+$]. found: 594.2430. λ$_{abs}$ (CH$_2$Cl$_2$, ε×10$^{-3}$) 400 (43) nm.

EXAMPLE 37

General procedure for the synthesis of 2,5-bis(arylethynyl)-1,4-bis(aryl)-1,4-dihydropyrrolo[3,2-b]pyrroles (35-39)

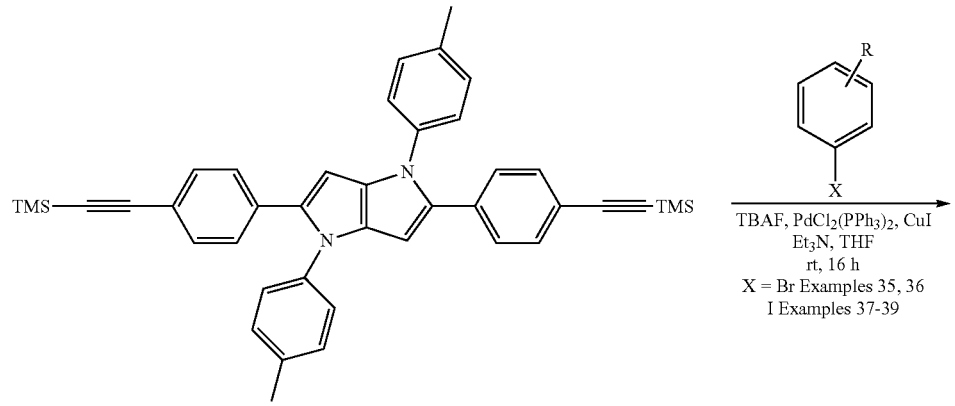

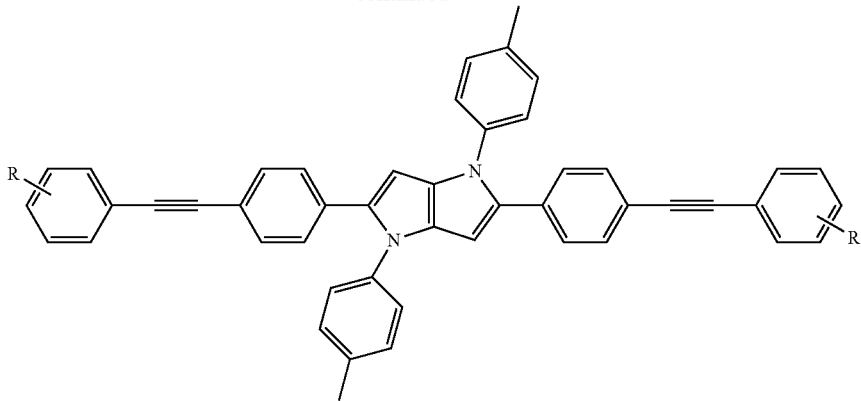

An oven-dried 25 ml Schlenk flask was charged with 1,4-bis(4-methylphenyl)-2,5-bis(4-((trimethylsilyl)ethynyl)phenyl)-1,4-dihydropyrrolo[3,2-b]pyrrole (16, 20 mg, 3.17×$10^{-5}$ mol), PdCl$_2$(PPh$_3$)$_2$ (2.2 mg, 3.17×$10^{-6}$ mol), CuI (0.6 mg, 3.17×$10^{-6}$ mol) and bromo- or iodoarene (6.317×$10^{-5}$ mol). Then anhydrous THF (0.5 ml) was added, followed by Et$_3$N (0.5 ml, 3.6 mmol). Reaction mixture were deoxygenated by freeze-pump-thaw cycles and purged with argon. TBAF (21 mg, 7.92×$10^{-6}$ mol) was added, and the reaction mixture was stirred for 16 h at room temperature under argon atmosphere. The crude mixture was filtered through celite and the solvent was distilled off. Purification using DCVC method afforded pure product.

The examples 38-42 present synthetic results of applied procedure—compounds 35-39.

EXAMPLE 38

2,5-bis(4-(4-cyanophenylethynyl)phenyl)-1,4-bis(4-methylphenyl)-1,4-dihydropyrrolo[3,2-b]pyrrole (35)

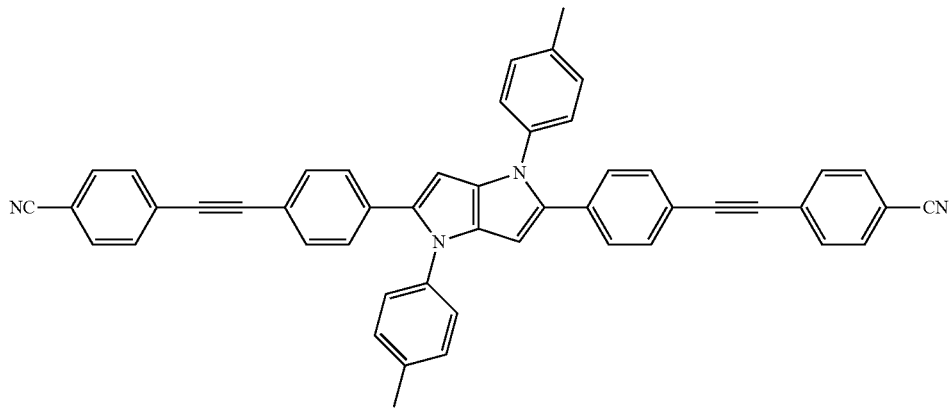 [SMILES: Cc1ccc(-n2c(-c3ccc(C#Cc4ccc(C#N)cc4)cc3)cc3c2cc(-c2ccc(C#Cc4ccc(C#N)cc4)cc2)n3-c2ccc(C)cc2)cc1]

Product was purified by means of DCVC method (SiO$_2$, hexanes/CH$_2$Cl$_2$, 4:1) afforded pure product as a yellow solid, 12 mg (56%). R$_f$=0.27 (SiO$_2$, hexanes/CH$_2$Cl$_2$, 1:1). Mp 313-314° C. (AcOEt, decomp.). $^1$H NMR (500 MHz, CDCl$_3$) δ 7.61 (AA'XX', 4H), 7.57 (AA'XX', 4H), 7.38 (AA'XX', 4H), 7.21 (AA'XX', 4H), 7.19 (m, 8H), 6.42 (s, 2H), 2.39 (s, 6H); $^{13}$C NMR (125 MHz, CDCl$_3$) δ 137.5, 136.1, 135.7, 134.5, 132.9, 132.2, 132.1, 131.8, 130.1, 128.5, 127.9, 125.4, 119.6, 118.6, 111.5, 95.2, 88.5, 21.2. HRMS (EI) calcd for C$_{50}$H$_{32}$N$_4$: 688.2627 [M$^+$]. found: 688.2596. λ$_{abs}$ (CH$_2$Cl$_2$, ε×$10^{-3}$) 428 (70) nm.

EXAMPLE 39

2,5-bis(4-(4-pentafluorothiophenyl)ethynylphenyl)-1,4-bis(4-methylphenyl)-1,4-dihydropyrrolo[3,2-b]pyrrole (36)

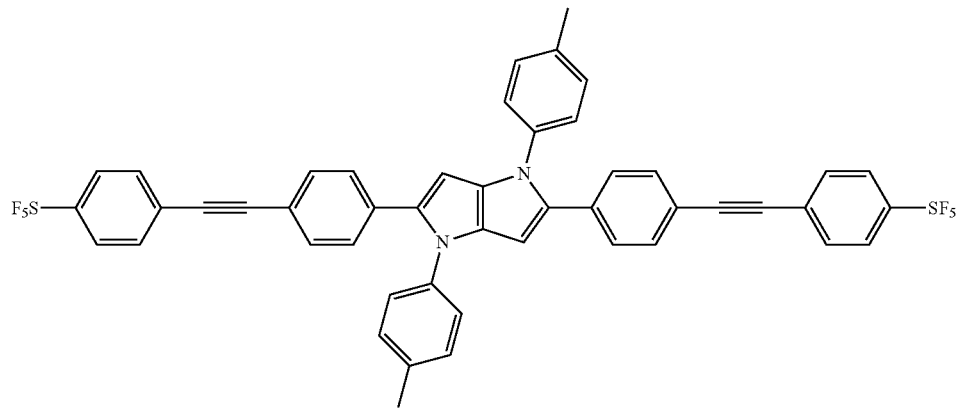

Purification using DCVC method (SiO$_2$, hexanes/CH$_2$Cl$_2$, 4:1) afforded pure product as a yellow solid, 6 mg (21%). R$_f$=0.72 (SiO$_2$, hexanes/CH$_2$Cl$_2$, 1:1). Mp 207-208° C. (AcOEt). $^1$H NMR (500 MHz, CDCl$_3$) δ 7.65 (AA'XX', 4H), 7.48 (AA'XX', 4H), 7.33 (AA'XX', 4H), 7.14 (AA'XX', 4H), 7.13-7.08 (m, 8H), 6.36 (s, 2H), 2.32 (s, 6H); $^{13}$C NMR (125 MHz, CDCl$_3$) δ 137.3, 135.9, 135.5, 134.2, 132.6, 131.6, 131.5, 129.9, 127.7, 127.1, 126.0, 125.2, 119.5, 95.0, 92.7, 87.9, 29.7, 21.0. HRMS (EI) calcd for C$_{48}$H$_{32}$F$_{10}$N$_2$S$_2$: 890.1847[M$^+$]. found: 890.1843. λ$_{abs}$ (CH$_2$Cl$_2$, ε×10$^{-3}$) 418 (45) nm.

EXAMPLE 40

2,5-bis(4-(4-trifluoromethyl)ethynylphenyl)-1,4-bis(4-methylphenyl)-1,4-dihydropyrrolo[3,2-b]pyrrole (37)

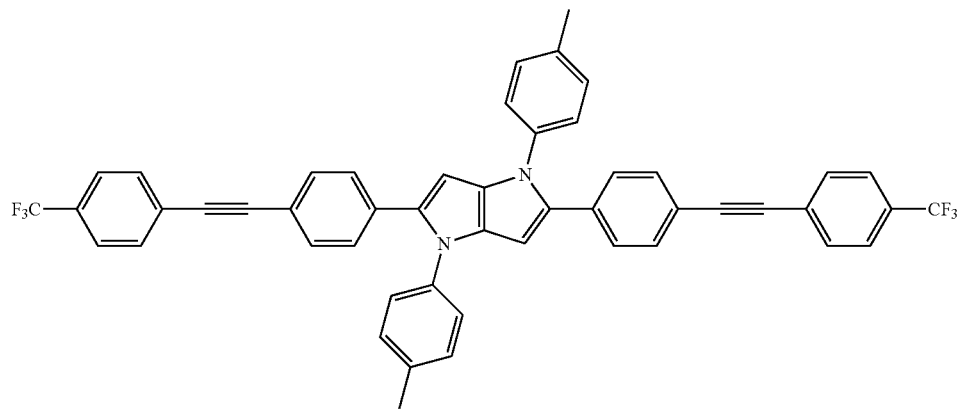

Purification using DCVC method (SiO$_2$, hexanes/CH$_2$Cl$_2$, 6:1) afforded pure product as a orange solid, 4 mg (15%). R$_f$=0.76 (SiO$_2$, hexanes/CH$_2$Cl$_2$, 1:1). Mp 347-348° C. (AcOEt, decomp.). $^1$H NMR (500 MHz, CDCl$_3$) δ 7.59 (s, 8H), 7.39 (AA'XX', 4H), 7.19 (m, 12H), 6.42 (s, 2H), 2.38 (s, 6H). $^{13}$C NMR (125 MHz, CDCl$_3$) δ 137.5, 136.0, 131.9, 130.1, 125.4, 125.4, 21.2. HRMS (EI) calcd for C$_{50}$H$_{32}$F$_6$N$_2$: 774.2470 [M$^+$]. found: 774.2461. λ$_{abs}$ (CH$_2$Cl$_2$, ε×10$^{-3}$) 414 (62) nm.

EXAMPLE 41

2,5-bis(4-(3,5-di(trifluoromethyl)ethynylphenyl)-1,4-bis(4-methylphenyl)-1,4-dihydropyrrolo[3,2-b]pyrrole (38)

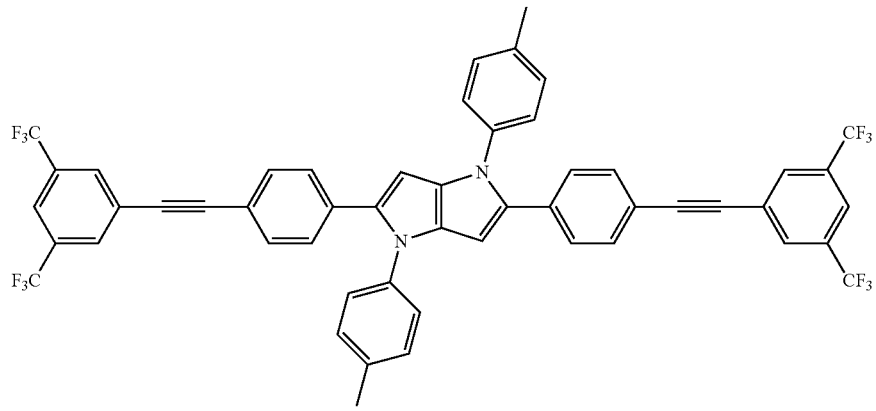 [SMILES: Cc1ccc(-n2c(-c3ccc(C#Cc4cc(C(F)(F)F)cc(C(F)(F)F)c4)cc3)cc3c2cc(-c2ccc(C#Cc4cc(C(F)(F)F)cc(C(F)(F)F)c4)cc2)n3-c2ccc(C)cc2)cc1]

Purification using DCVC method (SiO$_2$, hexanes/CH$_2$Cl$_2$, 8:1) afforded pure product as a yellow solid, 10 mg (33%). R$_f$=0.78 (SiO$_2$, hexanes/CH$_2$Cl$_2$, 1:1). Mp 316-317° C. (AcOEt). $^1$H NMR (500 MHz, CDCl$_3$) δ 7.92 (s, 4H), 7.80 (s, 2H), 7.40 (AA'XX', 4H), 7.23 (AA'XX', 4H), 7.20 (m, 8H), 6.45 (s, 2H), 2.39 (s, 6H); $^{13}$C NMR (125 MHz, CDCl$_3$) δ 137.4, 136.1, 134.6, 132.9, 132.2, 132.0, 131.8, 131.4, 130.1, 127.9, 125.9, 125.3, 124.2, 122.0, 119.1, 95.2, 93.3, 87.0, 21.2. HRMS (EI) calcd for C$_{52}$H$_{30}$F$_{12}$N$_2$: 910.2215 [M$^+$]. found: 910.2188. λ$_{abs}$ (CH$_2$Cl$_2$, ε×10$^{-3}$) 421 (67) nm.

EXAMPLE 42

2,5-bis(4-(methoxy)ethynylphenyl)-1,4-bis(4-methylphenyl)-1,4-dihydropyrrolo[3,2-b]pyrrole (39)

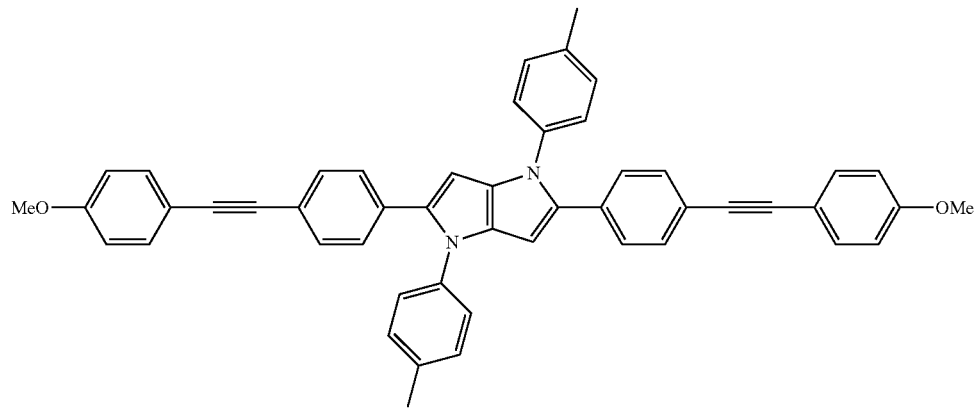 [SMILES: COc1ccc(C#Cc2ccc(-c3cc4c(cc(-c5ccc(C#Cc6ccc(OC)cc6)cc5)n4-c4ccc(C)cc4)n3-c3ccc(C)cc3)cc2)cc1]

Purification using DCVC method (SiO$_2$, hexanes/CH$_2$Cl$_2$, 3:1) afforded pure product as a yellow solid, 7 mg (30%). R$_f$=0.44 (SiO$_2$, hexanes/CH$_2$Cl$_2$, 1:1). Mp 315-316° C. (AcOEt). $^1$H NMR (500 MHz, CDCl$_3$) δ 7.44 (AA'XX', 4H), 7.35 (AA'XX', 4H), 7.18 (s, 12H), 6.87 (AA'XX', 4H), 6.40 (s, 2H), 3.82 (s, 6H), 2.38 (s, 6H); $^{13}$C NMR (125 MHz, CDCl$_3$) δ 159.7, 137.5, 135.8, 133.1, 131.3, 123.0, 129.2, 128.4, 127.8, 125.5, 125.3, 114.1, 55.5, 21.2. HRMS (EI) calcd for C$_{50}$H$_{38}$N$_2$O$_2$: 698.2933 [M$^+$]. found: 698.2955. λ$_{abs}$ (CH$_2$Cl$_2$, ε×10$^{-3}$) 401 (71) nm.

EXAMPLE 43

Optical Properties of Compounds Synthesized According to the Present Invention

Optical measurements were performed for compounds synthesized according to the present invention. For this purpose each compound was dissolved in CH$_2$Cl$_2$, unless otherwise noted, and absorption spectra were measured. The same solutions were exposed to monochromatic light with wavelength 325-345 nm and emission spectra were measured. Comparison with reference spectrum (quinine bisulfate (VI) in H$_2$SO$_4$, 0.5 M) gave the fluorescence quantum yield coefficient. All the measurements were performed at room temperature. Results are shown in Table 1.

TABLE 1

Spectroscopic properties of selected compounds.

| Cpd | λ$_{abs}$ [nm] | λ$_{em}$ [nm] | Stokes Shift [cm$^{-1}$] | Molar absorption coefficient ε$_{max}$ [M$^{-1}$ cm$^{-1}$] | Fluorescence quantum yield Φ$_{fl}$ |
|---|---|---|---|---|---|
| 2 | 348 | 410 | 4300 | 37 000 | 0.37 |
| 3 | 377 | 443 | 4000 | 14 000 | 0.51 |
| 5 | 405 | 459 | 3000 | 54 000 | 0.24 |
| 6 | 368 | 462 | 5500 | 33 000 | 0.17 |
| 9[a] | 348 | 412 | 4500 | 36 000 | 0.52 |

TABLE 1-continued

Spectroscopic properties of selected compounds.

| Cpd | $\lambda_{abs}$ [nm] | $\lambda_{em}$ [nm] | Stokes Shift [cm$^{-1}$] | Molar absorption coefficient $\varepsilon_{max}$ [M$^{-1}$ cm$^{-1}$] | Fluorescence quantum yield $\Phi_{fl}$ |
|---|---|---|---|---|---|
| 11 | 400 | 455 | 3000 | 49 000 | 0.78 |
| 12 | 345 | 400 | 4000 | 34 000 | 0.57 |
| 13 | 360 | — | — | 41 000 | — |
| 19 | 336 | 414 | 5600 | 28 000 | 0.62 |
| 22 | 399 | 454 | 3000 | 50 000 | 0.86 |
| 27 | 404 | 472 | 3600 | 40 000 | 0.57 |
| 29 | 381 | — | — | 45 000 | — |
| 30 | 395 | 463 | 3700 | 33 000 | 0.63 |
| 32 | 396 | 465 | 3800 | 36 000 | 0.64 |
| 33 | 400 | 474 | 3900 | 43 000 | 0.48 |
| 35 | 428 | 549 | 5200 | 70 000 | 0.22 |
| 36 | 418 | 523 | 4800 | 45 000 | 0.16 |
| 37 | 414 | 511 | 4600 | 62 000 | 0.42 |
| 38 | 421 | 522 | 4600 | 67 000 | 0.37 |
| 39 | 401 | 479 | 4100 | 71 000 | 0.53 |

[a]spectra measured in toluene

FIG. 1 shows fluorescence of selected compounds in solutions.

EXAMPLE 44

Electrochemical Properties of Compound According to the Invention

Figure 2:
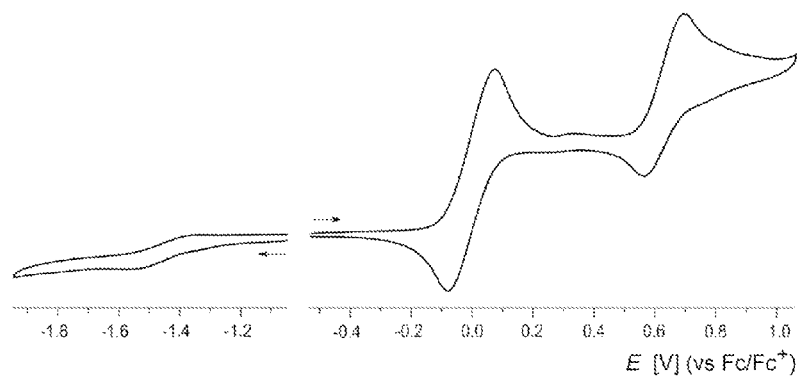
Figure 3:
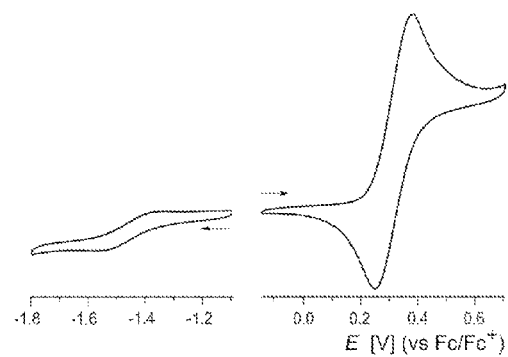

Electrochemistry of two compounds (19 and 32) has been studied via cyclic voltammetry (Table 2, FIG. 2-3). It was shown that some of these compounds have interesting behavior such as low oxidation potential and large HOMO-LUMO gap. This can be advantageous in such applications as bulk-heterojunction solar cells, organic field-effect transistors etc.

TABLE 2

Electrochemical data for compounds 19 and 32 vs. Fc/Fc$^+$).

| | $E^{1/2}_{ox1}$ [V] | $E^{1/2}_{ox2}$ [V] | $E^{1/2}_{red}$ [V] | HOMO-LUMO gap [eV] |
|---|---|---|---|---|
| 19 | −0.01 | 0.62 | −1.46 | 1.45 |
| 32 | 0.32 V | | −1.46 | 1.78 |

FIG. 2 shows a cyclic voltammetry for compound 19 and FIG. 3 the cyclic voltammetry for compound 32.

The invention claimed is:

1. A compound of formula (I):

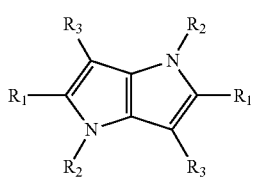

wherein $R_1$ and $R_3$ at each instance independently are hydrogen, alkyl, aryl, arylethynylaryl or heteroaryl, and $R_2$ at each instance independently are aryl, arylethynylaryl or heteroaryl;

with the proviso that the aryl is optionally substituted with one or more substituents selected from the group consisting of CN, CO$_2$Me, CO$_2$Et, SO$_3$H, CHO, CONH$_2$, F, Cl, Br, I, NO$_2$, OMe, OCH$_2$O, NH$_2$, NMe$_2$, and SF$_5$, and the arylethynylaryl is optionally substituted with one or more substituents selected from the group consisting of NO$_2$, CN, OMe, SO$_2$Me, SO$_3$H, F, Cl, Br, I, CHO, COOH, CONH$_2$, and SF$_5$;

with the proviso that when at least one $R_1$ is heteroaryl, the heteroaryl is a six-membered aromatic ring comprising at least one heteroatom selected from the group consisting of N, O, S and Se.

2. The compound according to claim 1, wherein at least one $R_3$ is H.

3. The compound according to claim 2, wherein $R_1$ and $R_2$ at each instance independently are an aryl or heteroaryl group, with the proviso that when at least one $R_1$ is heteroaryl, the heteroaryl is a six-membered aromatic ring comprising at least one heteroatom selected from the group consisting of N, O, S and Se.

4. A compound of formula (I):

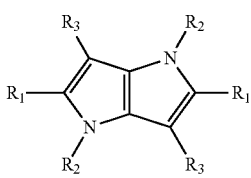

wherein $R_1$ and $R_2$ at each instance independently are phenyl, optionally substituted with one or more substituents selected from the group consisting of NO$_2$, CN, OMe, SO$_2$Me, SO$_3$H, F, Cl, Br, I, CHO, COOH, CONH$_2$ and SF$_5$;

$R_3$ at each instance independently are hydrogen, alkyl, aryl, arylethynylaryl or heteroaryl;

with the proviso that the aryl is optionally substituted with one or more substituents selected from the group consisting of CN, CO$_2$Me, CO$_2$Et, SO$_3$H, CHO, CONH$_2$, F, Cl, Br, I, NO$_2$, OMe, OCH$_2$O, NH$_2$, NMe$_2$, and SF$_5$, and the arylethynylaryl is optionally substituted with one or more substituents selected from the group consisting of NO$_2$, CN, OMe, SO$_2$Me, SO$_3$H, F, Cl, Br, I, CHO, COOH, CONH$_2$, and SF$_5$.

5. The compound according to claim 1, wherein the compound is represented by general formula (II):

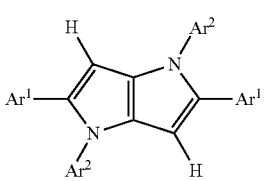

wherein Ar$^1$ and Ar$^2$ at each instance independently are aryl or heteroaryl, with the proviso that the aryl is optionally substituted with one or more substituents selected from the group consisting of CN, CO$_2$Me, CO$_2$Et, SO$_3$H, CHO, CONH$_2$, F, Cl, Br, I, NO$_2$, OMe, OCH$_2$O, NH$_2$, NMe$_2$, and SF$_5$, and with the proviso that when at least one Ar$^1$ is heteroaryl, the heteroaryl is a six-membered aromatic ring comprising at least one heteroatom selected from the group consisting of N, O, S and Se.

6. The compound according to claim 1, wherein the compound is represented by general formula III or IV:

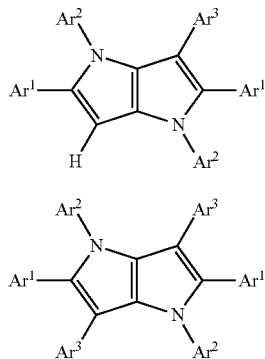

wherein Ar¹, Ar² and Ar³ at each instance independently are aryl or heteroaryl, with the proviso that the aryl is optionally substituted with one or more substituents selected from the group consisting of CN, $CO_2Me$, $CO_2Et$, $SO_3H$, CHO, $CONH_2$, F, Cl, Br, I, $NO_2$, OMe, $OCH_2O$, $NH_2$, $NMe_2$, and $SF_5$, and with the proviso that when at least one Ar¹ is heteroaryl, the heteroaryl is a six-membered aromatic ring comprising at least one heteroatom selected from the group consisting of N, O, S and Se.

7. The compound according to claim 1, wherein the compound is represented by general formula V:

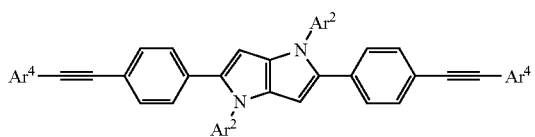

wherein Ar² and Ar⁴ at each instance independently are aryl or heteroaryl, with the proviso that the aryl is optionally substituted with one or more substituents selected from the group consisting of CN, $CO_2Me$, $CO_2Et$, $SO_3H$, CHO, $CONH_2$, F, Cl, Br, I, $NO_2$, OMe, $OCH_2O$, $NH_2$, $NMe_2$, and $SF_5$.

8. A compound selected from the group consisting of:
2,5-diphenyl 1,4-bis(4-methylphenyl)-1,4-dihydropyrrolo[3,2-b]pyrrole,
1,2,4,5-tetra(4-methylphenyl)-1,4-dihydropyrrolo[3,2-b]pyrrole,
2,5-di(naphthalen-1-yl)-1,4-bis(4-methylphenyl)-1,4-dihydropyrrolo[3,2-b]pyrrole,
2,5-di(anthracen-9-yl)-1,4-bis(4-octylphenyl)-1,4-dihydropyrrolo[3,2-b]pyrrole,
2,5-bis(4-cyanophenyl)-1,4-bis(4-methylphenyl)-1,4-dihydropyrrolo[3,2-b]pyrrole,
2,5-bis(3-cyanophenyl)-1,4-bis(4-methylphenyl)-1,4-dihydropyrrolo[3,2-b]pyrrole,
2,5-bis(2-cyanophenyl)-1,4-bis(4-methylphenyl)-1,4-dihydropyrrolo[3,2-b]pyrrole,
s(4-bromophenyl)-2,5-bis(4-methylphenyl)-1,4-dihydropyrrolo[3,2-b]pyrrole,
2,5-bis(4-methoxyphenyl)-1,4-bis(4-methylphenyl)-1,4-dihydropyrrolo[3,2-b]pyrrole,
2,5-bis(benzo[d][1,3]dioxol-5-yl)-1,4-bis(4-methylphenyl)-1,4-dihydropyrrolo[3,2-b]pyrrole,
1,4-bis(4-chlorophenyl)-2,5-bis(4-cyanophenyl)-1,4-dihydropyrrolo[3,2-b]pyrrole,
2,5-bis(4-fluorophenyl)-1,4-bis(4-methoxyphenyl)-1,4-dihydropyrrolo[3,2-b]pyrrole,
1,4-bis(4-nitrophenyl)-2,5-bis(4-methylphenyl)-1,4-dihydropyrrolo[3,2-b]pyrrole,
2,5-bis(3-nitrophenyl)-1,4-bis(4-octylphenyl)-1,4-dihydropyrrolo[3,2-b]pyrrole,
2,5-di(pyridin-3-yl)-1,4-bis(4-methylphenyl)-1,4-dihydropyrrolo[3,2-b]pyrrole,
1,4-bis(4-methylphenyl)-2,5-bis(4-((trimethylsilyl)ethynyl)phenyl)-1,4-dihydropyrrolo[3,2-b]pyrrole,
2,5-bis(2-bromophenyl)-1,4-bis(4-methylphenyl)-1,4-dihydropyrrolo[3,2-b]pyrrole,
2,5-bis(2-methoxyphenyl)-1,4-bis(4-methylphenyl)-1,4-dihydropyrrolo[3,2-b]pyrrole,
2,5-bis(2-(allyloxy)phenyl)-1,4-bis(4-methylphenyl)-1,4-dihydropyrrolo[3,2-b]pyrrole,
1,4-bis(4-methylphenyl)-2,5-bis(4-(pentafluoro-λ6-sulfanyl)phenyl)-1,4-dihydropyrrolo[3,2-b]pyrrole,
1,2,4,5-tetrakis(4-(pentafluoro-λ6-sulfanyl)phenyl)-1,4-dihydropyrrolo[3,2-b]pyrrole,
1,4-bis(4-bromophenyl)-2,5-bis(4-cyanophenyl)-1,4-dihydropyrrolo[3,2-b]pyrrole,
2,5-bis(4-bromo-2-nitrophenyl)-1,4-bis(4-hexylphenyl)-1,4-dihydropyrrolo[3,2-b]pyrrole,
2,5-bis(benzo[b]thiophen-2-yl)-bis(4-methylphenyl)-1,4-dihydropyrrolo[3,2-b]pyrrole,
2,5-di(benzofuran-2-yl)-1,4-bis(4-methylphenyl)-1,4-dihydropyrrolo[3,2-b]pyrrole,
1,4-bis(4-methylphenyl)-2,5-bis(thiazol-2-yl)-1,4-dihydropyrrolo[3,2-b]pyrrole,
2,5-bis(4-cyanophenyl)-3-(9,9-dioctyl-9H-fluoren-3-yl)-1,4-bis(4-methylphenyl)-dihydropyrrolo[3,2-b]pyrrole,
2,5-bis(4-cyanophenyl)-1,4-bis(4-methylphenyl)-3-(4-nitrophenyl)-dihydropyrrolo[3,2-b]pyrrole,
2,5-bis(4-cyanophenyl)-1,4-bis(4-methylphenyl)-3,6-bis(4-nitrophenyl)-dihydropyrrolo[3,2-b]pyrrole,
2,5-bis(4-cyanophenyl)-1,4-bis(4-methylphenyl)-3,6-bis(4-(pentafluoro-λ6-sulfanyl)phenyl)-1,4-dihydropyrrolo[3,2-b]pyrrole,
2,5-bis(4-cyanophenyl)-1,4-bis(4-methylphenyl)-3-(pyridin-3-yl)-1,4-dihydropyrrolo[3,2-b]pyrrole,
2,5-bis(4-cyanophenyl)-1,4-bis(4-methylphenyl)-3,6-di(pyridin-3-yl)-1,4-dihydropyrrolo[3,2-b]pyrrole,
2,3,5-tris(4-cyanophenyl)-1,4-bis(4-methylphenyl)-1,4-dihydropyrrolo[3,2-b]pyrrole,
2,5-bis(4-cyanophenyl)-3-(4-methoxyphenyl)-1,4-bis(4-methylphenyl)-1,4-dihydropyrrolo[3,2-b]pyrrole,
2,5-bis(4-(4-cyanoethynylphenyl)phenyl)-1,4-bis(4-methylphenyl)-1,4-dihydropyrrolo[3,2-b]pyrrole,
2,5-bis(4-(4-pentafluorothiophenyl)ethynylphenyl)-1,4-bis(4-methylphenyl)-1,4-dihydropyrrolo[3,2-b]pyrrole,
2,5-bis(4-(4-trifluoromethyl)ethynylphenyl)-1,4-bis(4-methylphenyl)-1,4-dihydropyrrolo[3,2-b]pyrrole,
2,5-bis(4-(3,5-di(trifluoromethyl)ethynylphenyl)-1,4-bis(4-methylphenyl)-1,4-dihydropyrrolo[3,2-b]pyrrole, and
2,5-bis(4-(methoxy)ethynylphenyl)-1,4-bis(4-methylphenyl)-1,4-dihydropyrrolo[3,2-b]pyrrole.

9. A process for the preparation of the compound of claim 5, represented by general formula (II):

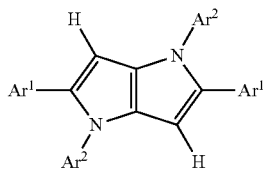

(II)

where Ar$^1$ and Ar$^2$ at each instance independently are aryl or heteroaryl, with the proviso that the aryl is optionally substituted with one or more substituents selected from the group consisting of CN, CO$_2$Me, CO$_2$Et, SO$_3$H, CHO, CONH$_2$, F, Cl, Br, I, NO$_2$, OMe, OCH$_2$O, NH$_2$, NMe$_2$, and SF$_5$, and with the proviso that when at least one Ar$^1$ is heteroaryl, the heteroaryl is a six-membered aromatic ring comprising at least one heteroatom selected from the group consisting of N, O, S and Se;

the process comprising reacting butane-2,3-dione with an arylaldehyde of formula Ar$^1$CHO and an arylamine of formula Ar$^2$NH$_2$ in acidic conditions, and afterwards isolating the compound of formula (II).

10. The process according to claim 9, wherein the reacting is carried out in an acetic acid.

11. The process according to claim 9, wherein the reacting is carried out at a temperature above 50° C.

12. The process according to claim 9, further comprising precipitating the compound of formula (II) from a cooled reaction mixture.

13. The process according to claim 9, wherein the reacting is performed in the presence of a Brønsted acid as a catalyst.

14. The process according to claim 9, wherein the reacting is performed in the presence of an acid with pK$_a$<2 as a catalyst.

15. The compound according to claim 1, wherein both instances of R$_3$ are H.

16. The process according to claim 9, wherein the reacting is carried out in a glacial acetic acid.

17. The process according to claim 9, wherein the reacting is carried out at a temperature around 100° C.

18. The process according to claim 9, wherein the reacting is performed in the presence of an arylsulfonic acid, as a catalyst.

19. The process according to claim 9, wherein the reacting is performed in the presence of p-toluenosulfonic acid or benzenesulfonic acid, as a catalyst.

20. The compound according to claim 4, wherein at least one R$_3$ is H.

* * * * *